(12) United States Patent
Loerz et al.

(10) Patent No.: US 6,897,358 B2
(45) Date of Patent: May 24, 2005

(54) NUCLEIC ACID MOLECULES ENCODING WHEAT ENZYMES INVOLVED IN STARCH SYNTHESIS

(75) Inventors: Horst Loerz, Hamburg (DE); Stephanie Luetticke, Hamburg (DE); Gernot Abel, Kobenhaven (DK); Ulrich Genschel, Hamburg (DE)

(73) Assignee: Bayer CropScience GmbH, Frankfurt am Main (DE)

( * ) Notice: Subject to any disclaimer, the term of this patent is extended or adjusted under 35 U.S.C. 154(b) by 0 days.

(21) Appl. No.: 10/238,091

(22) Filed: Sep. 10, 2002

(65) Prior Publication Data

US 2003/0093834 A1 May 15, 2003

Related U.S. Application Data

(62) Division of application No. 09/674,817, filed as application No. PCT/EP99/03141 on May 7, 1999.

(30) Foreign Application Priority Data

May 8, 1998 (DE) .......................................... 198 20 608

(51) Int. Cl.[7] .................. C12N 15/29; C12N 15/56; C12N 15/82; C12N 15/87; A01H 5/00
(52) U.S. Cl. ...................... 800/284; 800/278; 800/285; 800/286; 800/290; 800/298; 435/419; 435/320.1; 435/210; 536/23.2; 536/23.6
(58) Field of Search ................................. 800/298, 278, 800/285, 284, 286, 290; 435/419, 210, 320.1, 468; 536/23.2, 23.6, 23.1, 24.5

(56) References Cited

FOREIGN PATENT DOCUMENTS

WO    WO 96/03513    2/1996
WO    WO 99/14314    3/1999

OTHER PUBLICATIONS

Kossmann et al (1995, Carbohydrate Bioengineering, S.B. Petersen, B. Svensson and S Pedersen (Eds.) pp. 271–278).*
Willmitzer et al (1993, Starch synthesis in transgenic plants, In Plant Polymeric Carbohydrates; International Symposium Meuser, F., D.J. Manners and W. Seibel (Eds) pp. 33–39).*
Colliver et al (1997, Plant Mol. Biol. 35:509–522).*
Montgomery et al (Trends in Genetics, Jul. 1998, 14(7):255–258).*
Bowie et al, Science 247:1306–1310, 1990.*
McConnell et al, Nature 411 (6838):709–713, 2001.*
Fourgoux–Nicol et al (1999, Plant Molecular Biology 40 :857–872.*
Kossmann et al (1995, Carbohydrate Bioengineering, S.B. Petersen, B. Svensson and S Pedersen (Eds). pp. 271–278).*
Willmitzer et al (1993, Starch synthesis in transgenic plants, In Plant Polymeric Carbohydrates; International Symposium Meuser, F., D.J. Manners and W. Seibel (Eds) pp. 33–39).*
Bowie et al, Science 247:1306–1310, 1990.*
McConnell et al, Nature 411 (6838):709–713, 2001.*
Fourgoux–Nicol et al (1999, Plant Molecular Biology 40 :857–872).*
Reeck et al., 1987, Cell 50:667.*
Colliver et al (1997, Plant Mol. Biol. 35:509–522).*
Montgomery et al (Trends in Genetics, Jul. 1998, 14(7):255–258).*
James et al., "Characterization of the Maize Gene sugary1, a Determinant of Starch Composition in Kernels", The Plant Cell, vol. 7, 417–429, Apr. 1995.
James et al., "Zea mays sulp (Sugary1) mRNA, partial cds", EMBL Nucleotide Sequence, U18908, Apr. 19, 1995, (XP002084161).
Plant Gene Register PGR 97–187, Genomic Nucleotide Sequence of a Full–length Wild–type Allele of the Maize Surgaryl (Sul) Gene (Accession No. AF030882).

* cited by examiner

*Primary Examiner*—David T. Fox
*Assistant Examiner*—Stuart F. Baum
(74) *Attorney, Agent, or Firm*—Frommer Lawrence & Haug LLP

(57) ABSTRACT

The invention relates to nucleic acid molecules which code for enzymes and which are involved in the synthesis of starch in plants. These enzymes concern isoamylases derived from wheat. The invention also relates to vectors and host cells which contain the described nucleic acid molecules, especially transformed plant cells and plants which can be regenerated therefrom, which exhibit an increased or reduced activity of the inventive isoamylases.

11 Claims, No Drawings

```
                          SEQUENCE LISTING (1) GENERAL INFORMATION:

(iii) NUMBER OF SEQUENCES: 134

(2) INFORMATION FOR SEQ ID NO: 1:

(i) SEQUENCE CHARACTERISTICS:
           (A) LENGTH: 6 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Xaa
           (B) LOCATION: 1
           (D) OTHER INFORMATION: /label= variable
               /note= "Represents Ala, Arg, Asp, Gly, Lys, Ser,
               or Thr"

(ix) FEATURE:
           (A) NAME/KEY: Xaa
           (B) LOCATION: 2
           (D) OTHER INFORMATION: /label= variable
               /note= "Represents Ile, Leu, Met, Phe or Trp"

(ix) FEATURE:
           (A) NAME/KEY: Xaa
           (B) LOCATION: 3
           (D) OTHER INFORMATION: /label= variable
               /note= "Represents Leu or Phe"

(ix) FEATURE:
           (A) NAME/KEY: Xaa
           (B) LOCATION: 6
           (D) OTHER INFORMATION: /label= variable
               /note= "Represents Ala or Gly"

(xi) SEQUENCE DESCRIPTION: SEQ ID NO: 1:

Xaa Xaa Xaa Xaa Xaa Xaa
1               5

(2) INFORMATION FOR SEQ ID NO: 2:

(i) SEQUENCE CHARACTERISTICS:
           (A) LENGTH: 32 amino acids
           (B) TYPE: amino acid
           (C) STRANDEDNESS: single
           (D) TOPOLOGY: linear (ii) MOLECULE TYPE: peptide (ix) FEATURE:
           (A) NAME/KEY: Xaa
           (B) LOCATION: 1
           (D) OTHER INFORMATION: /label= Dpr
               /note= 2,3-diaminopropionic is acetyl cysteine (ix) FEATURE:
           (A) NAME/KEY: Xaa
           (B) LOCATION: 2
```

```
        (D) OTHER INFORMATION: /label= Ahe
            /note= 2-amino heptanoic is butyl alanine (xi) SEQUENCE DESCRIPTION: SEQ ID NO: 2:

Xaa Xaa Glu Thr His Val Thr Gly Gly Ser Ala Gly His Thr Val Ser
1               5                   10                  15

Gly Phe Val Ser Leu Leu Ala Pro Gly Ala Lys Gln Asn Val Gln Leu
                20                  25                  30

(2) INFORMATION FOR SEQ ID NO: 3:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 3:

Val Ser Leu Leu Ala
1               5

(2) INFORMATION FOR SEQ ID NO: 4:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 4:

Ser Leu Leu Ala Pro Gly Ala
1               5

(2) INFORMATION FOR SEQ ID NO: 5:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Leu Ala Pro Gly Ala
1               5

(2) INFORMATION FOR SEQ ID NO: 6:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa
        (B) LOCATION: 7
        (D) OTHER INFORMATION: /label= variable
            /note= "Represents Ala, Pro or Ser"

(xi) SEQUENCE DESCRIPTION: SEQ ID NO: 6:

Ser Leu Leu Xaa Xaa Gly Xaa
```

-continued 1          5

(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa
        (B) LOCATION: 7
        (D) OTHER INFORMATION: /label= variable
            /note= "Represents Ala, Pro or Ser"

(xi) SEQUENCE DESCRIPTION: SEQ ID NO: 7:

Ser Leu Phe Xaa Xaa Gly Xaa
1          5

(2) INFORMATION FOR SEQ ID NO: 8:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa
        (B) LOCATION: 1
        (D) OTHER INFORMATION: /label= variable
            /note= "Represents Any Amino Acid"

(ix) FEATURE:
        (A) NAME/KEY: Xaa
        (B) LOCATION: 3
        (D) OTHER INFORMATION: /label= variable
            /note= "Represents Any Amino Acid"

(ix) FEATURE:
        (A) NAME/KEY: Xaa
        (B) LOCATION: 8
        (D) OTHER INFORMATION: /label= variable
            /note= "Represents Any Amino Acid"

(ix) FEATURE:
        (A) NAME/KEY: Xaa
        (B) LOCATION: 14
        (D) OTHER INFORMATION: /label= variable
            /note= "Represents Any Amino Acid"

(ix) FEATURE:
        (A) NAME/KEY: Xaa
        (B) LOCATION: 16
        (D) OTHER INFORMATION: /label= variable
            /note= "Represents Any Amino Acid"

(ix) FEATURE:
        (A) NAME/KEY: Xaa
        (B) LOCATION: 17
        (D) OTHER INFORMATION: /label= variable
            /note= "Represents Any Amino Acid"

(ix) FEATURE:
        (A) NAME/KEY: Xaa
        (B) LOCATION: 21
        (D) OTHER INFORMATION: /label= variable
            /note= "Represents Any Amino Acid"

(ix) FEATURE:
        (A) NAME/KEY: Xaa

```
        (B) LOCATION: 22
        (D) OTHER INFORMATION: /label= variable
            /note= "Represents Any Amino Acid"

(ix) FEATURE:
        (A) NAME/KEY: Xaa
        (B) LOCATION: 24
        (D) OTHER INFORMATION: /label= variable
            /note= "Represents Any Amino Acid"

(ix) FEATURE:
        (A) NAME/KEY: Xaa
        (B) LOCATION: 27
        (D) OTHER INFORMATION: /label= variable
            /note= "Represents Any Amino Acid"

(xi) SEQUENCE DESCRIPTION: SEQ ID NO: 8:

Xaa Thr Xaa Val Thr Gly Gly Xaa Ala Ala Arg Thr Thr Xaa Gly Xaa
1               5                   10                  15

Xaa Ser Leu Phe Xaa Xaa Gly Xaa Ser Gln Xaa Ile Gln Leu Ile
            20                  25                  30

(2) INFORMATION FOR SEQ ID NO: 9:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 9:

Ala Thr Tyr Ala Thr Gly Ala Ala Gln Gly His Ala Thr Asn Ser Phe
1               5                   10                  15

Val Ser Leu Phe Arg Ser Gly Ala Ser Gln Asn Leu Lys Leu Val
            20                  25                  30

(2) INFORMATION FOR SEQ ID NO: 10:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 10:

Ser Thr Gln Val Thr Gly Gly Gln Ala Ala His Thr Val Arg Gly Val
1               5                   10                  15

Ala Ser Ile Phe Ser Pro Gly Ser Arg Gln Asp Ile Ser Leu Ile
            20                  25                  30

(2) INFORMATION FOR SEQ ID NO: 11:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 11:

Ser Thr Arg Val Thr Gly Gly Gln Gln Gly Arg Ala Val His Gly Ile
1               5                   10                  15

Ala Ser Leu Phe Ser Leu Gly Ala Ser Gln Lys Ile Gln Leu Val
```

20              25              30

(2) INFORMATION FOR SEQ ID NO: 12:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

Ser Thr His Val Met Gly Ala Gln Gln Gly Arg Val Ala Lys Gly Phe
1               5                   10                  15

Thr Ser Leu Phe Gly Pro Gly Pro Ala Gln Lys Ile Gly Leu Ile
            20              25                  30

(2) INFORMATION FOR SEQ ID NO: 13:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

Ser Thr His Val Thr Gly Ala Val Gln Gly His Ser Ile Arg Gly Leu
1               5                   10                  15

Thr Ser Leu Phe Thr Ser Gly Pro Ala Gln Lys Ile Gln Leu Val
            20              25                  30

(2) INFORMATION FOR SEQ ID NO: 14:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Glu Thr His Val Thr Gly Gly Ile Ala Ala Lys Thr Thr Ala Ser Leu
1               5                   10                  15

Thr Gly Leu Phe Asn Leu Gly Ala Lys Gln Asn Ile Gln Leu Ile
            20              25                  30

(2) INFORMATION FOR SEQ ID NO: 15:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

Glu Thr His Val Thr Gly Gly Asn Ala Gly Arg Ala Ala Ala Gly Ile
1               5                   10                  15

Ala Gly Leu Phe Thr Leu Gly Ala Lys Gln Asn Val Gln Leu Ile
            20              25                  30

(2) INFORMATION FOR SEQ ID NO: 16:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 16:

```
Gln Thr Arg Val Thr Gly Gly Thr Ala Ala Gln Ser Thr Ala Arg Ile
1               5                  10                  15

Ala Gly Leu Phe Ser Leu Gly Ala Arg Gln Asn Ile Gln Leu Ile
            20                  25                  30
```

(2) INFORMATION FOR SEQ ID NO: 17:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Gln Thr His Val Met Gly Gly Thr Ala Gly Arg Asn Ala Tyr Gly Leu
1               5                  10                  15

Thr Ser Phe Leu Ser Val Gly Ala Ser Gln Lys Ile Gln Leu Ile
            20                  25                  30
```

(2) INFORMATION FOR SEQ ID NO: 18:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 18:

```
Glu Thr His Val Met Gly Gly Ala Ala Ser Ser Thr Thr Tyr Arg Phe
1               5                  10                  15

Ala Ser Leu Phe Thr Ser Gly Pro Ala Gln Lys Ile Gln Leu Val
            20                  25                  30
```

(2) INFORMATION FOR SEQ ID NO: 19:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

```
Glu Thr His Val Thr Gly Gly Ser Ala Ala Ser Thr Thr Ala Thr Phe
1               5                  10                  15

Ser Lys Leu Phe Met Pro Gly Ala Ser Gln Asn Ile Gln Leu Ile
            20                  25                  30
```

(2) INFORMATION FOR SEQ ID NO: 20:

(i) SEQUENCE CHARACTERISTICS:

(A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 20:

Gly Thr Thr Arg Val Gly Gly Ala Ala Arg Thr Thr Ser Ser Phe
1               5                   10                  15

Ala Ser Leu Leu Thr His Gly Pro Ser Gln Asn Ile Gln Leu Val
            20                  25                  30

(2) INFORMATION FOR SEQ ID NO: 21:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 21:

Gly Thr His Val Thr Gly Gly Ala Ala Ala Arg Asp Ala Phe Arg Phe
1               5                   10                  15

Ser Ser Leu Phe Thr Arg Gly Pro Ser Gln Asn Ile Gln Leu Ile
            20                  25                  30

(2) INFORMATION FOR SEQ ID NO: 22:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Ala Thr Asn Met Thr Gly Gly Ala Pro Ala Arg Thr Thr Tyr Lys Leu
1               5                   10                  15

Thr Thr Leu Phe Ser Tyr Gly Ala Ser Gln Lys Ile Gln Leu Ile
            20                  25                  30

(2) INFORMATION FOR SEQ ID NO: 23:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 23:

His Asn His Val Thr Gly Gly Thr Ser Ala Arg Asn Thr Phe Gly Ile
1               5                   10                  15

Thr Thr Leu Phe Thr Gln Gly Pro Ser Gln Lys Leu Gln Leu Val
            20                  25                  30

(2) INFORMATION FOR SEQ ID NO: 24:

(i) SEQUENCE CHARACTERISTICS:
        (A) LENGTH: 31 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 24:

Gly Thr His Val Thr Gly Gly Ala Ala Ala Arg Asn Ala His Ser Leu
1               5                  10                  15

Thr Ser Leu Leu Ala Pro Gly Ala Ser Gln Lys Ile Gln Leu Ile
            20                  25                  30

(2) INFORMATION FOR SEQ ID NO: 25:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 25:

Thr Thr Arg Val Ser Gly Gly Thr Ala Ala His Thr Thr Ala Gly Leu
1               5                  10                  15

Thr Ser Leu Phe Ser Pro Gly Pro Arg Gln Asn Ile His Leu Val
            20                  25                  30

(2) INFORMATION FOR SEQ ID NO: 26:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 26:

Thr Thr His Val Ser Gly Gly Thr Ala Gly Arg Thr Thr Ala Ser Leu
1               5                  10                  15

Thr Ser Phe Phe Ala Pro Gly Ala Ser Gln Arg Ile Gln Leu Val
            20                  25                  30

(2) INFORMATION FOR SEQ ID NO: 27:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 27:

Thr Thr His Val Thr Gly Gly Ala Thr Gly His Thr Thr Ser Gly Ile
1               5                  10                  15

Ala Ser Leu Phe Leu Pro Gly Ala Ser Gln Lys Ile Gln Leu Ile
            20                  25                  30

(2) INFORMATION FOR SEQ ID NO: 28:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 28:

Asp Thr Tyr Ala Ser Gly Gly Ala Gln Gly Arg Ser Thr Leu Gly Phe
1               5                   10                  15

Thr Ser Leu Phe Thr Pro Gly Ala Ser Gln Lys Ile Gln Leu Ile
            20                  25                  30

(2) INFORMATION FOR SEQ ID NO: 29:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 29:

Asp Thr Tyr Ala Ser Gly Gly Ala Ala Gly Arg Ala Thr Tyr Gly Ile
1               5                   10                  15

Thr Ser Leu Phe Ala Pro Gly Ala Ser Gln Asn Ile Gln Leu Ile
            20                  25                  30

(2) INFORMATION FOR SEQ ID NO: 30:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 30:

Arg Thr Tyr Ala Ser Gly Gly Ala Ala Gly Arg Thr Thr His Gly Phe
1               5                   10                  15

Thr Ser Leu Phe Ser Thr Gly Ala Arg Gln Asn Ile Gln Leu Ile
            20                  25                  30

(2) INFORMATION FOR SEQ ID NO: 31:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 31:

Gln Thr Tyr Val Thr Gly Gly Lys Ala Ala Gln Thr Val Ser Gly Phe
1               5                   10                  15

Thr Gly Leu Phe Ser Ser Gly Pro Ser Gln Lys Ile Gln Leu Ile
            20                  25                  30

(2) INFORMATION FOR SEQ ID NO: 32:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 32:

-continued

```
Asp Thr Tyr Val Ser Gly Gly Ala Ala Ala Arg Ser Ile Ser Gly Phe
1               5                   10                  15

Thr Ser Leu Phe Thr Pro Gly Ala Ser Gln Lys Ile Gln Leu Val
            20                  25                  30
```

(2) INFORMATION FOR SEQ ID NO: 33:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 33:

```
Ser Thr Tyr Val Thr Gly Gly Glu Ala Ser Arg Thr Thr Arg Gly Phe
1               5                   10                  15

Ala Ser Leu Phe Thr Leu Gly Ser Ser Gln Lys Ile Gln Leu Ile
            20                  25                  30
```

(2) INFORMATION FOR SEQ ID NO: 34:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 34:

```
Asn Thr Tyr Val Thr Gly Gly Ser Ala Gly Arg Ala Val Ala Gly Phe
1               5                   10                  15

Ala Gly Leu Leu Gln Pro Gly Ala Lys Gln Asn Val Gln Leu Ile
            20                  25                  30
```

(2) INFORMATION FOR SEQ ID NO: 35:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 35:

```
His Thr Arg Val Thr Gly Gly Gln Val Ala Phe Arg Thr His Gly Leu
1               5                   10                  15

Val Ser Leu Phe Thr Gln Gly Pro Ser Gln Lys Ile Gln Leu Val
            20                  25                  30
```

(2) INFORMATION FOR SEQ ID NO: 36:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 36:

```
His Thr His Val Thr Gly Gly Arg Val Ala Ser Ser Thr Gln Ser Leu
1               5                   10                  15
```

```
Val Ser Trp Leu Ser Gln Gly Pro Ser Gln Lys Ile Gln Leu Val
            20                  25                  30
```

(2) INFORMATION FOR SEQ ID NO: 37:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 37:

```
His Thr Arg Val Thr Gly Gly Val Gln Gly His Val Thr Ser Thr Leu
1               5                   10                  15
Thr Ser Leu Phe Arg Pro Gly Ala Ser Gln Lys Ile Gln Leu Val
            20                  25                  30
```

(2) INFORMATION FOR SEQ ID NO: 38:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 38:

```
Asn Thr Arg Val Thr Gly Gly Val Gln Gly Arg Asp Thr Ser Gly Leu
1               5                   10                  15
Val Ser Leu Phe Ser Leu Gly Pro Ser Gln Lys Ile Gln Leu Val
            20                  25                  30
```

(2) INFORMATION FOR SEQ ID NO: 39:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 39:

```
Asp Thr His Val Thr Gly Gly Ala Gln Ala Lys Thr Thr Asn Arg Leu
1               5                   10                  15
Val Ser Met Phe Ala Ser Gly Pro Ser Gln Lys Ile Gln Leu Ile
            20                  25                  30
```

(2) INFORMATION FOR SEQ ID NO: 40:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 40:

```
Glu Thr His Val Thr Gly Gly Ala Ser Ala Arg Thr Thr Gln Arg Phe
1               5                   10                  15
Thr Ser Phe Phe Asp Leu Gly Pro Ser Gln Lys Ile Gln Leu Val
            20                  25                  30
```

(2) INFORMATION FOR SEQ ID NO: 41:

(i) SEQUENCE CHARACTERISTICS:
       (A) LENGTH: 31 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 41:

Thr Thr Tyr Met Thr Gly Gly Ala Asn Ala Arg Thr Thr Gln Gly Phe
1               5                  10                  15

Val Ser Leu Phe Thr Pro Gly Pro Ala Gln Lys Ile Gln Leu Val
            20                  25                  30

(2) INFORMATION FOR SEQ ID NO: 42:

(i) SEQUENCE CHARACTERISTICS:
       (A) LENGTH: 31 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 42:

Glu Thr His Val Thr Gly Gly Thr Ser Ala Arg Thr Thr Gln Gly Phe
1               5                  10                  15

Val Ser Leu Phe Ser Ala Gly Ala Ser Gln Lys Ile Gln Leu Val
            20                  25                  30

(2) INFORMATION FOR SEQ ID NO: 43:

(i) SEQUENCE CHARACTERISTICS:
       (A) LENGTH: 31 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 43:

Gly Thr His Val Thr Gly Gly Gln Ala Ala Arg Thr Thr Gln Ser Phe
1               5                  10                  15

Thr Ser Leu Phe Ser Pro Gly Pro Gln Gln Lys Ile Gln Leu Ile
            20                  25                  30

(2) INFORMATION FOR SEQ ID NO: 44:

(i) SEQUENCE CHARACTERISTICS:
       (A) LENGTH: 31 amino acids
       (B) TYPE: amino acid
       (C) STRANDEDNESS: single
       (D) TOPOLOGY: linear (ii) MOLECULE TYPE: peptide (xi) SEQUENCE DESCRIPTION: SEQ ID NO: 44:

Arg Thr His Val Thr Gly Gly Lys Ala Ala His Thr Thr Lys Gly Phe
1               5                  10                  15

Ala Ser Leu Phe Thr Pro Gly Pro Ser Gln Asn Ile Gln Leu Ile
            20                  25                  30

(2) INFORMATION FOR SEQ ID NO: 45:

```
    (i) SEQUENCE CHARACTERISTICS:
         (A) LENGTH: 31 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 45:

Glu Thr Arg Val Thr Gly Ala Val Gln Gly His Gly Ala Leu Gly Leu
1               5                  10                  15

Ala Ser Leu Phe Thr Pro Gly Pro Ser Gln Lys Ile Gln Leu Ile
            20                  25                  30

(2) INFORMATION FOR SEQ ID NO: 46:

(i) SEQUENCE CHARACTERISTICS:
         (A) LENGTH: 31 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 46:

Glu Thr Arg Val Thr Gly Ala Ile Ala Gly Arg Thr Ala Ser Ser Phe
1               5                  10                  15

Ala Gly Leu Phe Thr Ser Gly Ala Ser Gln Lys Ile Gln Leu Val
            20                  25                  30

(2) INFORMATION FOR SEQ ID NO: 47:

(i) SEQUENCE CHARACTERISTICS:
         (A) LENGTH: 31 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 47:

Glu Thr Arg Val Thr Gly Gln Gln Val Gly Arg Thr Thr Gln Ser Leu
1               5                  10                  15

Thr Ser Leu Phe Thr Pro Gly Pro Ser Gln Thr Ile Gln Leu Ile
            20                  25                  30

(2) INFORMATION FOR SEQ ID NO: 48:

(i) SEQUENCE CHARACTERISTICS:
         (A) LENGTH: 31 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO: 48:

Gln Thr Arg Val Thr Gly Ala Gln Val Gly Arg Thr Thr Ser Ser Leu
1               5                  10                  15

Thr Ser Leu Phe Thr Pro Gly Pro Ser Gln Asn Ile Gln Leu Val
            20                  25                  30

(2) INFORMATION FOR SEQ ID NO: 49:

(i) SEQUENCE CHARACTERISTICS:
         (A) LENGTH: 31 amino acids
         (B) TYPE: amino acid
```

(C) STRANDEDNESS: single
        (D) TOPOLOGY: linear (ii) MOLECULE TYPE: peptide (xi) SEQUENCE DESCRIPTION: SEQ ID NO: 49:

Arg Thr Gln Val Thr Gly Ala Gln Ala Gly His Thr Thr Ser Gly Leu
1               5                   10                  15

Ala Ser Leu Phe Thr Pro Gly Pro Ser Gln Lys Ile Gln Leu Val
            20                  25                  30

(2) INFORMATION FOR SEQ ID NO: 50:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 50:

Glu Thr His Val Thr Gly Gly Ser Ala Gly His Thr Val Ser Gly Phe
1               5                   10                  15

Val Ser Leu Leu Ala Pro Gly Ala Lys Gln Asn Val Gln Leu Ile
            20                  25                  30

(2) INFORMATION FOR SEQ ID NO: 51:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Glu Thr His Val Thr Gly Gly Ser Ala Gly His Thr Val Thr Gly Ile
1               5                   10                  15

Ala Ser Leu Phe Thr Ser Gly Ala Lys Gln Asn Ile Gln Leu Ile
            20                  25                  30

(2) INFORMATION FOR SEQ ID NO: 52:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Ser Thr His Val Thr Gly Gly Thr Ala Ala His Thr Val Ala Gly Phe
1               5                   10                  15

Ser Ser Leu Phe Thr Val Gly Pro Lys Gln Asn Ile Gln Leu Ile
            20                  25                  30

(2) INFORMATION FOR SEQ ID NO: 53:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 53:

Glu Thr His Val Thr Gly Gly Ala Ala Ala Tyr Thr Ala Ala Gly Leu
1               5                   10                  15

Ala Ser Leu Phe Thr Ser Gly Ala Lys Gln Asn Ile Gln Leu Ile
            20                  25                  30

(2) INFORMATION FOR SEQ ID NO: 54:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 54:

Glu Thr His Val Thr Gly Gly Ser Ala Gly Arg Thr Thr Ala Gly Leu
1               5                   10                  15

Val Gly Leu Leu Thr Pro Gly Ala Lys Gln Asn Ile Gln Leu Ile
            20                  25                  30

(2) INFORMATION FOR SEQ ID NO: 55:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 55:

Gly Thr His Val Thr Gly Gly Ser Ala Gly Arg Ala Thr Ala Gly Ile
1               5                   10                  15

Ala Gly Leu Leu Thr Pro Gly Ala Arg Gln Asn Ile Gln Leu Val
            20                  25                  30

(2) INFORMATION FOR SEQ ID NO: 56:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 56:

Lys Thr His Val Thr Gly Gly Ser Ala Ala Arg Thr Thr Ser Gly Ile
1               5                   10                  15

Ala Ser Leu Leu Thr Pro Gly Ala Lys Gln Asn Val Gln Leu Ile
            20                  25                  30

(2) INFORMATION FOR SEQ ID NO: 57:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 57:

-continued

```
Lys Thr Tyr Val Thr Gly Gly Ser Gln Ala Gln Ala Thr Phe Gly Phe
1               5                   10                  15

Thr Ser Leu Leu Gln Gln Gly Ala Lys Gln Asn Ile Gln Leu Ile
            20                  25                  30
```

(2) INFORMATION FOR SEQ ID NO: 58:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 58:

```
Glu Thr Thr Val Thr Gly Gly Ser Ala Ala His Gly Ala Leu Gly Ile
1               5                   10                  15

Ala Ser Leu Phe Asn Gln Gly Ala Arg Gln Asn Ile Gln Leu Ile
            20                  25                  30
```

(2) INFORMATION FOR SEQ ID NO: 59:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 59:

```
Glu Thr Tyr Val Thr Gly Gly Ala Ser Ala Arg Ser Thr Phe Thr Leu
1               5                   10                  15

Val Gly Leu Phe Lys Gln Gly Ser Gln Gln Asn Ile Gln Leu Val
            20                  25                  30
```

(2) INFORMATION FOR SEQ ID NO: 60:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 60:

```
Gln Thr Tyr Val Ser Gly Gly Ser Ser Gly Arg Thr Thr Ser Gly Leu
1               5                   10                  15

Val Ser Ile Phe Ser Pro Gly Ala Ser Gln Asn Leu Gln Leu Ile
            20                  25                  30
```

(2) INFORMATION FOR SEQ ID NO: 61:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 61:

```
Glu Thr Tyr Val Ser Gly Gly Ala Ala Ala Gln Thr Thr Ala Arg Phe
1               5                   10                  15
```

```
Ala Gly Phe Phe Gln Ser Gly Ala Lys Gln Asn Ile Gln Leu Ile
        20                  25                  30

(2) INFORMATION FOR SEQ ID NO: 62:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 62:

Glu Thr Tyr Val Ser Gly Gly Ser Ala Ala Gln Thr Thr Ala Gly Phe
1               5                   10                  15

Val Arg Leu Phe Glu Thr Gly Pro Lys Gln Asn Ile Gln Leu Ile
        20                  25                  30

(2) INFORMATION FOR SEQ ID NO: 63:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 63:

Ser Thr Tyr Val Ser Gly Gly Ala Gln Ala Arg Ala Ala Gln Gly Ile
1               5                   10                  15

Thr Ser Leu Phe Ser Arg Gly Ser Ser Gln Lys Ile Gln Leu Val
        20                  25                  30

(2) INFORMATION FOR SEQ ID NO: 64:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 64:

Ser Thr Tyr Val Thr Gly Gly Thr Gln Gly Arg Ala Ala Ser Gly Leu
1               5                   10                  15

Thr Ser Leu Phe Ser Ala Gly Ala Ser Gln Asn Ile Gln Leu Ile
        20                  25                  30

(2) INFORMATION FOR SEQ ID NO: 65:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 65:

Asn Thr Tyr Val Ser Gly Gly Thr Ala Gly His Thr Gly His Gly Leu
1               5                   10                  15

Thr Ala Leu Phe Ser Pro Gly Ala Ser Gln Asn Ile Gln Leu Ile
        20                  25                  30
```

(2) INFORMATION FOR SEQ ID NO: 66:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 66:

```
Ser Thr Ile Val Ser Gly Gly Thr Val Ala Arg Thr Thr His Ser Leu
1               5                   10                  15

Ala Ser Leu Phe Thr Gln Gly Ala Ser Gln Lys Ile Gln Leu Ile
            20                  25                  30
```

(2) INFORMATION FOR SEQ ID NO: 67:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

```
Glu Thr Tyr Thr Ser Gly Gly Ala Ala Ser His Thr Thr Ser Thr Leu
1               5                   10                  15

Ala Ser Leu Phe Ser Pro Gly Ala Ser Gln Arg Ile Gln Leu Val
            20                  25                  30
```

(2) INFORMATION FOR SEQ ID NO: 68:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 68:

```
His Thr Leu Thr Thr Gly Gly His Ala Ala Arg Leu Thr Ser Gly Phe
1               5                   10                  15

Ala Gly Leu Phe Thr Pro Gly Pro Ser Gln Arg Ile Gln Leu Ile
            20                  25                  30
```

(2) INFORMATION FOR SEQ ID NO: 69:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 69:

```
Glu Thr Ile Val Ser Gly Gly Gln Ala Ala Arg Ala Met Ser Gly Leu
1               5                   10                  15

Val Ser Leu Phe Thr Pro Gly Ala Lys Gln Asn Ile Gln Leu Ile
            20                  25                  30
```

(2) INFORMATION FOR SEQ ID NO: 70:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 70:

Glu Thr Tyr Thr Ser Gly Gly Asn Ala Gly His Thr Met Thr Gly Ile
1               5                   10                  15

Val Arg Phe Phe Ala Pro Gly Pro Lys Gln Asn Val His Leu Ile
            20                  25                  30

(2) INFORMATION FOR SEQ ID NO: 71:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

Thr Thr Tyr Thr Thr Gly Gly Asn Ala Ala Arg Thr Thr Gln Ala Leu
1               5                   10                  15

Thr Ser Phe Phe Ser Pro Gly Ala Lys Gln Asp Ile Gln Leu Ile
            20                  25                  30

(2) INFORMATION FOR SEQ ID NO: 72:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 72:

Glu Thr Tyr Thr Thr Gly Gly Ser Thr Ala Arg Thr Thr Gln Gly Leu
1               5                   10                  15

Val Ser Leu Phe Ser Arg Gly Ala Lys Gln Asp Ile Gln Leu Ile
            20                  25                  30

(2) INFORMATION FOR SEQ ID NO: 73:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 73:

Ala Thr Tyr Thr Ser Gly Gly Ser Ala Ala Arg Thr Thr Gln Gly Phe
1               5                   10                  15

Ala Ser Leu Phe Ser Leu Gly Ser Gln Gln Lys Ile Gln Leu Val
            20                  25                  30

(2) INFORMATION FOR SEQ ID NO: 74:

(i) SEQUENCE CHARACTERISTICS:
        (A) LENGTH: 31 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 74:

Ala Thr Tyr Thr Thr Gly Gly Ser Val Ala Arg Thr Thr His Gly Phe
1               5                   10                  15

Ser Ser Leu Phe Ser Gln Gly Ala Lys Gln Asn Ile Gln Leu Ile
            20                  25                  30

(2) INFORMATION FOR SEQ ID NO: 75:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 75:

Val Thr Tyr Thr Thr Gly Gly Ser Gln Ala Arg His Thr Gln Ser Val
1               5                   10                  15

Thr Ser Phe Phe Thr Gln Gly Pro Ala Gln Arg Ile Gln Leu Ile
            20                  25                  30

(2) INFORMATION FOR SEQ ID NO: 76:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 76:

His Thr Tyr Thr Thr Gly Gly Thr Val Ala Arg Ser Thr Gln Gly Leu
1               5                   10                  15

Val Gly Phe Leu Ser Pro Gly Pro Ser Gln Asn Ile Gln Leu Ile
            20                  25                  30

(2) INFORMATION FOR SEQ ID NO: 77:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 77:

Thr Thr Tyr Val Ser Val Gly His Ala Ser Gln Thr Thr Arg Arg Val
1               5                   10                  15

Ala Ser Phe Phe Ser Pro Gly Ser Ala Gln Lys Ile Gln Leu Val
            20                  25                  30

(2) INFORMATION FOR SEQ ID NO: 78:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 78:

Thr Thr Thr Val Ser Gly Gly His Ala Ser Gln Ile Thr Arg Gly Val
1               5                   10                  15

Thr Ser Phe Phe Ser Pro Gly Ser Ala Gln Lys Ile Gln Leu Val
            20                  25                  30

(2) INFORMATION FOR SEQ ID NO: 79:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 79:

Lys Thr Ser Leu Thr Gly Val Thr Arg Ala Arg Ala Ala Ala Arg Leu
1               5                   10                  15

Thr Ala Leu Phe Ser Ser Gly Pro Ser Gln Arg Ile Gln Leu Ile
            20                  25                  30

(2) INFORMATION FOR SEQ ID NO: 80:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 80:

Gly Thr Ser Leu Thr Gly Gly Ala Arg Ala Arg Ala Ala Ser Gly Leu
1               5                   10                  15

Ala Gly Leu Phe Ser Ser Gly Pro Ser Gln Arg Ile Gln Leu Ile
            20                  25                  30

(2) INFORMATION FOR SEQ ID NO: 81:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 81:

Val Thr Gln Val Ser Pro Pro Gln Ala Gly Tyr Thr Thr Ser Val Leu
1               5                   10                  15

Thr Gly Ile Leu Ser Pro Gly Ala Lys Gln Asn Ile Gln Leu Val
            20                  25                  30

(2) INFORMATION FOR SEQ ID NO: 82:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 82:

Val Thr Gln Val Ser Gly Gly Gln Ala Gly Tyr Thr Thr Ser Val Leu
1               5                   10                  15

Thr Gly Ile Leu Ser Pro Gly Ala Lys Gln Asn Ile Gln Leu Val
            20                  25                  30

(2) INFORMATION FOR SEQ ID NO: 83:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 83:

Gly Thr Tyr Thr Val Gly Gly Ala Ser Ala Phe Thr Thr Ser Arg Leu
1               5                   10                  15

Thr Ser Leu Phe Ala Leu Gly Pro Ser Gln Arg Ile Gln Leu Val
            20                  25                  30

(2) INFORMATION FOR SEQ ID NO: 84:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 84:

Asn Thr His Thr Val Gly Gly Thr Glu Gly Phe Ala Thr Gln Arg Leu
1               5                   10                  15

Thr Ser Leu Phe Ala Leu Gly Pro Ser Gln Lys Ile Gln Leu Ile
            20                  25                  30

(2) INFORMATION FOR SEQ ID NO: 85:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 85:

Ser Thr Arg Thr Ala Gly Gly Ala Gln Ala Phe Asn Thr Tyr Gly Val
1               5                   10                  15

Ala Ser Ile Phe Ser Pro Gly Pro Ser Gln Arg Ile Gln Leu Val
            20                  25                  30

(2) INFORMATION FOR SEQ ID NO: 86:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 86:

Gln Thr His Thr Val Gly Gly Ser Thr Ala His Asn Ala Arg Thr Leu

```
                1               5                   10                  15
Thr Gly Met Phe Ser Leu Gly Ala Arg Gln Lys Ile Gln Leu Ile
            20                  25                  30

(2) INFORMATION FOR SEQ ID NO: 87:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 87:

Asn Thr Arg Thr Val Ala Gly Ser Ala Ala Thr Thr Arg Gly Phe
1               5                   10                  15
Thr Ser Met Phe Ser Ser Gly Ser Lys Gln Asn Leu Gln Leu Ile
            20                  25                  30

(2) INFORMATION FOR SEQ ID NO: 88:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 88:

Gln Thr Arg Thr Val Gly Gly Gln Val Gly His Ser Val Arg Gly Phe
1               5                   10                  15
Thr Ser Leu Phe Ser Ala Gly Ser Ala Gln Asn Ile Gln Leu Ile
            20                  25                  30

(2) INFORMATION FOR SEQ ID NO: 89:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 89:

Glu Thr His Thr Thr Gly Ala Val Ser Gly His Thr Thr Asn Val Leu
1               5                   10                  15
Thr Ser Leu Phe Ser Ser Gly Ser Ser Gln Asn Ile Gln Leu Ile
            20                  25                  30

(2) INFORMATION FOR SEQ ID NO: 90:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 90:

Val Thr Arg Thr Thr Gly Glu Val Ala Ala Arg Thr Ala Asn Thr Phe
1               5                   10                  15
Ala Ser Leu Phe Thr Thr Gly Pro Ser Gln Asn Ile Gln Leu Ile
```

20 25 30

(2) INFORMATION FOR SEQ ID NO: 91:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 91:

Thr Thr Tyr Ser Ser Gly Gln Glu Ala Gly Arg Thr Val Ala Gly Phe
1            5                   10                15

Ala Gly Leu Phe Thr Thr Gly Ala Lys Gln Asn Leu Tyr Leu Ile
           20                25               30

(2) INFORMATION FOR SEQ ID NO: 92:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 92:

Ser Thr Ser Val Val Gly Gly Arg Gln Ala Ser Ala Thr Phe Arg Phe
1            5                   10                15

Thr Ser Phe Phe Ser Arg Gly Pro Thr Gln Glu Ile Lys Leu Ile
           20                25               30

(2) INFORMATION FOR SEQ ID NO: 93:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 93:

Asn Thr Tyr Thr Thr Ala Gly Ser Met Ala Gln Ser Ile Tyr Arg Leu
1            5                   10                15

Thr Asp Ile Phe Ser Thr Gly Pro Ser Gln Lys Leu Gln Leu Val
           20                25               30

(2) INFORMATION FOR SEQ ID NO: 94:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 94:

Arg Thr Ile Leu Met Ala Gly Arg Gln Ala Glu Val Thr Gln Ser Phe
1            5                   10                15

Pro Gly Leu Phe Ser Leu Ala Pro Ser Gln Lys Ile His Leu Ile
           20                25               30

```
(2) INFORMATION FOR SEQ ID NO: 95:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 95:

Asp Thr Tyr Ala Thr Gly Gly Ser Val Ala Ser Ile Met Ala Gly Ile
1               5                   10                  15

Ala Arg Phe Phe Ser Pro Gly Ala Arg Gln Asp Ile Gln Leu Ile
            20                  25                  30

(2) INFORMATION FOR SEQ ID NO: 96:

(i) SEQUENCE CHARACTERISTICS:
        (A) LENGTH: 30 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 96:

Glu Thr Tyr Ala Thr Gly Ala Ser Ala Gly His Asp Val Ser Ser Phe
1               5                   10                  15

Ala Arg Leu Phe Ala Pro Gly Ala Arg Gln Asn Ile Gln Ile
            20                  25                  30

(2) INFORMATION FOR SEQ ID NO: 97:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 97:

Glu Thr His Arg Thr Gly Gly Ser Ala Ala Arg Ser Thr Ala Gly Val
1               5                   10                  15

Ala Ser Leu Phe Thr Pro Gly Ala Arg Gln Asn Ile Gln Leu Ile
            20                  25                  30

(2) INFORMATION FOR SEQ ID NO: 98:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 98:

Asn Thr Arg Ala Val Gly Met Val Gln Ser Arg Thr Thr Tyr Ala Leu
1               5                   10                  15

Thr Ser Leu Phe Asp Ser Gly Ala Ala Gln Lys Leu Gln Leu Val
            20                  25                  30

(2) INFORMATION FOR SEQ ID NO: 99:

(i) SEQUENCE CHARACTERISTICS:
```

(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 99:

```
Glu Thr His Val Thr Gly Gly Ser Ala Gly Arg Thr Thr Ala Gly Leu
1               5                   10                  15
Val Gly Leu Leu Thr Pro Gly Ala Lys Gln Asn Ile Gln Leu Ile
            20                  25                  30
```

(2) INFORMATION FOR SEQ ID NO: 100:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 100:

```
Glu Thr His Val Thr Gly Gly Ser Ala Gly Arg Ser Val Leu Gly Ile
1               5                   10                  15
Ser Phe Leu Thr Arg Gly Pro Lys Gln Asn Ile Gln Leu Ile
            20                  25                  30
```

(2) INFORMATION FOR SEQ ID NO: 101:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 101:

```
Glu Thr Tyr Thr Ser Gly Gly Ala Ala Ser His Thr Thr Ser Thr Leu
1               5                   10                  15
Ala Ser Leu Phe Ser Pro Gly Ala Ser Gln Arg Ile Gln Leu Val
            20                  25                  30
```

(2) INFORMATION FOR SEQ ID NO: 102:

(i) SEQUENCE CHARACTERISTICS:
(A) LENGTH: 31 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO: 102:

```
Ala Thr Tyr Thr Ser Gly Gly Val Ala Ser His Thr Thr Ser Arg Phe
1               5                   10                  15
Thr Ser Leu Phe Ser Ser Gly Ala Ser Gln Arg Ile Gln Leu Val
            20                  25                  30
```

(2) INFORMATION FOR SEQ ID NO: 103:

(i) SEQUENCE CHARACTERISTICS:
(A) LENGTH: 31 amino acids
(B) TYPE: amino acid
(C) STRANDEDNESS: single (D) TOPOLOGY: linear (ii) MOLECULE TYPE: peptide (xi) SEQUENCE DESCRIPTION: SEQ ID NO: 103:

Ala Thr Tyr Thr Ser Gly Ala Val Ala Ser His Thr Thr Ser Arg Phe
1               5                   10                  15

Thr Ser Phe Phe Ser Ser Gly Ala Ser Gln Arg Ile Gln Leu Val
            20                  25                  30

(2) INFORMATION FOR SEQ ID NO: 104:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 104:

Ala Thr Tyr Thr Ser Gly Ala Val Ala Ser His Thr Thr Ser Arg Phe
1               5                   10                  15

Thr Ser Leu Phe Ser Ser Gly Ala Ser Gln Arg Ile Gln Leu Val
            20                  25                  30

(2) INFORMATION FOR SEQ ID NO: 105:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 105:

Ala Thr Tyr Thr Ser Gly Ala Val Ala Ser His Thr Thr Ser Gly Phe
1               5                   10                  15

Thr Ser Leu Phe Ser Ser Gly Ala Ser Gln Arg Ile Gln Leu Val
            20                  25                  30

(2) INFORMATION FOR SEQ ID NO: 106:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 106:

Glu Thr Tyr Thr Ser Gly Arg Val Ala Gly His Thr Thr Ser Gly Phe
1               5                   10                  15

Thr Ser Leu Phe Ser Ser Gly Ala Ser Gln Arg Ile Gln Leu Val
            20                  25                  30

(2) INFORMATION FOR SEQ ID NO: 107:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 107:

Ala Thr Tyr Thr Ser Gly Gly Val Ala Gly Arg Thr Thr Ser Gly
1               5                   10                  15

Phe Thr Ser Leu Phe Ser Ser Gly Ala Ser Gln Lys Ile Gln Leu Val
            20                  25                  30

(2) INFORMATION FOR SEQ ID NO: 108:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 108:

Glu Thr His Thr Thr Gly Arg Val Ala Gly His Thr Thr Ser Arg Phe
1               5                   10                  15

Thr Ser Leu Phe Ser Ser Gly Ala Ser Gln Lys Ile Gln Leu Val
            20                  25                  30

(2) INFORMATION FOR SEQ ID NO: 109:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 109:

Glu Thr His Thr Thr Gly Arg Val Val Gly His Thr Thr Ser Gly
1               5                   10                  15

Phe Thr Ser Leu Phe Ser Ser Gly Ala Ser Gln Lys Ile Gln Leu Val
            20                  25                  30

(2) INFORMATION FOR SEQ ID NO: 110:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 110:

Glu Thr His Thr Thr Gly Arg Val Ala Gly Arg Thr Thr Ser Gly Phe
1               5                   10                  15

Thr Ser Leu Phe Ser Ser Gly Ala Ser Gln Lys Ile Gln Leu Val
            20                  25                  30

(2) INFORMATION FOR SEQ ID NO: 111:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 111:

Thr Thr Tyr Thr Ser Gly Gly Val Ala Gly Arg Thr Thr Ser Gly
1               5                   10                  15

Phe Thr Ser Leu Phe Ser Ser Gly Ala Ser Gln Lys Ile Gln Leu Val
                20                  25                  30

(2) INFORMATION FOR SEQ ID NO: 112:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 112:

Lys Thr Tyr Thr Ser Gly Gly Ala Ala Ser His Thr Thr Ser Arg
                5                   10                  15

Phe Thr Ser Leu Phe Ser Pro Gly Ala Ser Gln Arg Ile Gln Leu Val
                20                  25                  30

(2) INFORMATION FOR SEQ ID NO: 113:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 113:

Ser Thr Arg Val Thr Gly Gly Gln Gln Gly Arg Ala Val His Gly Ile
1               5                   10                  15

Ala Ser Leu Phe Ser Leu Gly Ala Ser Gln Lys Ile Gln Leu Val
                20                  25                  30

(2) INFORMATION FOR SEQ ID NO: 114:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 114:

Ser Thr Arg Val Thr Gly Gly Gln Gln Gly Arg Ala Val Gln Gly Phe
1               5                   10                  15

Ala Ser Leu Phe Arg Leu Gly Ala Ser Gln Glu Ile Gln Leu Val
                20                  25                  30

(2) INFORMATION FOR SEQ ID NO: 115:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 115:

Ser Thr Arg Val Thr Gly Gly Gln Gln Gly Arg Ala Val His Gly Ile
1               5                   10                  15

```
Ala Ser Leu Phe Ser Leu Gly Ala Ser Gln Lys Asn Gln Leu Val
            20                  25                  30
```

(2) INFORMATION FOR SEQ ID NO: 116:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 116:

```
Ser Thr Arg Val Thr Gly Gly Gln Gln Gly His Ala Ala His Ser Leu
1               5                   10                  15
Thr Ser Leu Phe Arg Leu Gly Ala Ser Gln Asn Ile Gln Leu Val
            20                  25                  30
```

(2) INFORMATION FOR SEQ ID NO: 117:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 117:

```
Asn Thr Arg Val Thr Gly Gly Arg Gln Gly Arg Ala Ala His Ser Leu
1               5                   10                  15
Thr Ser Leu Phe Ser Pro Gly Ala Ser Gln Asn Ile Gln Leu Val
            20                  25                  30
```

(2) INFORMATION FOR SEQ ID NO: 118:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 118:

```
Gly Thr Arg Val Thr Gly Gly Arg Gln Gly Arg Ala Ala His Ser Leu
1               5                   10                  15
Thr Ser Leu Phe Ser Pro Gly Ala Ser Glu Asn Ile Arg Leu Val
            20                  25                  30
```

(2) INFORMATION FOR SEQ ID NO: 119:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 119:

```
Ser Thr Arg Val Ser Gly Gly Gln Gln Gly Arg Ala Ala His Ser Leu
1               5                   10                  15
Thr Ser Leu Phe Thr Leu Gly Ala Ser Gln Asn Ile Gln Leu Val
            20                  25                  30
```

(2) INFORMATION FOR SEQ ID NO: 120:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 120:

```
Ser Thr His Val Thr Gly Ala Leu Gln Gly Arg Ala Ala Tyr Gly Ile
1               5                   10                  15
Thr Ser Phe Leu Ser His Gly Pro Ser Gln Lys Ile Gln Leu Val
            20                  25                  30
```

(2) INFORMATION FOR SEQ ID NO: 121:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 121:

```
Ser Thr Gln Val Met Gly Gly Gln Gln Gly Arg Ala Ala Tyr Ser Leu
1               5                   10                  15
Ala Ser Leu Leu Ser Pro Gly Ala Asn Gln Lys Ile Gln Leu Val
            20                  25                  30
```

(2) INFORMATION FOR SEQ ID NO: 122:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 122:

```
Ser Thr Gln Val Met Gly Gly Gln Gln Gly Arg Ala Ala Tyr Ser Leu
1               5                   10                  15
Ala Ser Leu Leu Gly Pro Gly Ala Ser Gln Lys Ile Gln Leu Val
            20                  25                  30
```

(2) INFORMATION FOR SEQ ID NO: 123:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 123:

```
Ser Thr Gln Val Met Gly Gly Gln Gln Gly Arg Ala Ala Tyr Ser Leu
1               5                   10                  15
Ala Ser Leu Leu Ser Pro Gly Ala Ser Gln Lys Ile Gln Leu Val
            20                  25                  30
```

(2) INFORMATION FOR SEQ ID NO: 124:

(i) SEQUENCE CHARACTERISTICS:
    (A) LENGTH: 31 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO: 124:

Arg Thr Arg Thr Val Gly Gly Gln Val Gly His Ser Val Arg Gly Phe
1               5                   10                  15

Thr Ser Leu Phe Ser Ala Gly Ser Ala Gln Asn Ile Gln Leu Ile
            20                  25                  30

(2) INFORMATION FOR SEQ ID NO: 125:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 125:

Gln Thr Arg Thr Val Gly Gly Gln Val Gly His Ser Val Arg Gly Phe
1               5                   10                  15

Thr Ser Leu Phe Ser Ala Gly Ser Ala Gln Asn Ile Gln Leu Ile
            20                  25                  30

(2) INFORMATION FOR SEQ ID NO: 126:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 126:

Gln Thr Arg Thr Val Gly Gly Gln Val Gly His Ser Val Arg Gly Phe
1               5                   10                  15

Thr Ser Leu Phe Ser Ala Gly Ser Ala Gln Asp Ile Gln Leu Ile
            20                  25                  30

(2) INFORMATION FOR SEQ ID NO: 127:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 127:

Gln Thr Arg Thr Val Gly Gly Gln Val Gly His Ser Val Arg Gly Phe
1               5                   10                  15

Thr Ser Leu Leu Ser Ala Gly Ser Ala Gln Asn Ile Gln Leu Ile
            20                  25                  30

(2) INFORMATION FOR SEQ ID NO: 128:

(i) SEQUENCE CHARACTERISTICS:
        (A) LENGTH: 31 amino acids
        (B) TYPE: amino acid

```
        (C) STRANDEDNESS: single
        (D) TOPOLOGY: linear (ii) MOLECULE TYPE: peptide (xi) SEQUENCE DESCRIPTION: SEQ ID NO: 128:

Gln Thr Arg Thr Val Gly Gly Gln Val Gly His Ser Val Arg Gly Leu
1               5                   10                  15

Thr Ser Leu Phe Ser Ala Gly Ser Ala Gln Asn Ile Gln Leu Ile
            20                  25                  30

(2) INFORMATION FOR SEQ ID NO: 129:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 129:

Gln Thr Arg Thr Val Gly Gly Gln Met Gly His Gly Val Arg Gly Leu
1               5                   10                  15

Thr Ser Leu Phe Ser Ala Gly Ser Ala Arg Asn Ile Gln Leu Ile
            20                  25                  30

(2) INFORMATION FOR SEQ ID NO: 130:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 130:

Gln Thr His Thr Val Gly Gly Gln Met Gly His Gly Val Arg Gly Leu
1               5                   10                  15

Thr Ser Leu Phe Ser Ala Gly Ser Ala Gln Asn Ile Gln Leu Ile
            20                  25                  30

(2) INFORMATION FOR SEQ ID NO: 131:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 131:

Gln Thr His Thr Val Gly Gly Gln Met Gly His Gly Val Arg Gly Leu
1               5                   10                  15

Thr Asn Leu Phe Ser Ala Gly Ser Ala Gln Asn Ile Gln Leu Ile
            20                  25                  30

(2) INFORMATION FOR SEQ ID NO: 132:

(i) SEQUENCE CHARACTERISTICS:
        (A) LENGTH: 24 amino acids
        (B) TYPE: amino acid
        (C) STRANDEDNESS: single
        (D) TOPOLOGY: linear
```

-continued (ii) MOLECULE TYPE: peptide (xi) SEQUENCE DESCRIPTION: SEQ ID NO: 132:

Glu Thr His Val Thr Gly Gly Ser Ala Gly His Thr Val Ser Gly Phe
1               5                   10                  15

Val Ser Leu Leu Ala Pro Gly Ala
            20

(2) INFORMATION FOR SEQ ID NO: 133:

(i) SEQUENCE CHARACTERISTICS:
        (A) LENGTH: 31 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Xaa
        (B) LOCATION: 1
        (D) OTHER INFORMATION: /label=Ahe
            /note=2-amino heptanoic is butyl alanine (xi) SEQUENCE DESCRIPTION: SEQ ID NO: 133:

Xaa Glu Thr His Val Thr Gly Gly Ser Ala Gly His Thr Val Ser Gl
1               5                   10                  15

Phe Val Ser Leu Leu Ala Pro Gly Ala Lys Gln Asn Val Gln Leu
            20                  25                  30

(2) INFORMATION FOR SEQ ID NO: 134:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 134:

Ser Leu Phe Xaa Xaa Gly
1           5

NUCLEIC ACID MOLECULES ENCODING WHEAT ENZYMES INVOLVED IN STARCH SYNTHESIS

This application is a divisional application of U.S. application Ser. No. 09/674,817, filed Nov. 6,2000, which was a National Phase entry under 35 U.S.C. §371 of PCT International Application No. PCT/EP99/03141, filed May 7, 1999, published in German on Nov. 18, 1999 as WO 99/58690, and claiming priority from German application 19820608.9, filed May 8, 1998. Each of the foregoing applications, and each document cited or referenced in each of the foregoing applications and during the prosecution of each of the foregoing applications ("application cited documents"), and each document referenced or cited in each of the application cited documents, and each document cited or referenced in this application ("herein cited documents") and each document cited or referenced in each of the herein cited documents, as well as all documents of Applicants during prosecution of each of the foregoing applications, are all hereby incorporated herein by reference.

The present invention relates to nucleic acid molecules which encode a wheat enzyme involved in starch synthesis in plants. This enzyme is an isoamylase.

The invention furthermore relates to vectors, host cells, plant cells and plants comprising the nucleic acid molecules according to the invention.

Furthermore, there are described methods for the generation of transgenic plants which, owing to the introduction of nucleic acid molecules according to the invention, synthesize starch with altered characteristics.

BACKGROUND OF THE INVENTION

In view of the increasing importance attributed lately to plant constituents as renewable raw materials, one of the objects of biotechnology research addresses the adaptation of these plant raw materials to the needs of the processing industries. Moreover, to allow renewable raw materials to be used in as many fields as possible, a wide diversity of materials must be generated.

Apart from oils, fats and proteins, polysaccharides constitute the important renewable raw materials from plants. Apart from cellulose, starch—which is one of the most important storage substances in higher plants—takes a central position amongst the polysaccharides. In this context, wheat is one of the most important crop plants since it provides approximately 20% of the total starch production in the European Community.

The polysaccharide starch is a polymer of chemically uniform units, the glucose molecules. However, it is a highly complex mixture of different molecule types which differ with regard to their degree of polymerization, the occurrence of branching of the glucose chains and their chain lengths, which, in addition, may be derivatized, for example phosphorylated. Starch therefore does not constitute a uniform raw material. In particular, a distinction is made between amylose starch, an essentially unbranched polymer of alpha-1,4-glycosidically linked glucose molecules, and amylopectin starch, which, in turn, constitutes a complex mixture of glucose chains with various branchings. The branchings occur by the occurrence of additional alpha-1,6-glycosidic linkages. In wheat, amylose starch makes up approximately 11 to 37% of the starch synthesized.

To allow suitable starches to be used in the widest possible manner for the widest possible range of industrial needs, it is desirable to provide plants which are capable of synthesizing modified starches which are particularly well suited to various purposes. One possibility of providing such plants is to employ plant-breeding measures. However, since wheat is polyploid in character (tetra- and hexaploid), the exertion of influence by plant breeding proves to be very difficult. A "waxy" (amylose-free) wheat was generated only recently by crossing naturally occurring mutants (Nakamura et al., Mol. Gen. Genet. 248 (1995), 253–259).

An alternative to plant-breeding methods is the specific modification of starch-producing plants by recombinant methods. However, prerequisites are the identification and characterization of the enzymes which are involved in starch synthesis and/or starch modification and the isolation of the nucleic acid molecules encoding these enzymes.

The biochemical pathways which lead to the synthesis of starch are essentially known. Starch synthesis in plant cells takes place in the plastids. In photosynthetically active tissue, these plastids are the chloroplasts and in photosynthetically inactive, starch-storing tissue are amyloplasts.

A further specific alteration of the degree of branching of starch synthesized in plants with the aid of recombinant methods still requires identification of DNA sequences, which encode enzymes involved in starch metabolism, in particular in the introduction or degradation of branching within the starch molecules.

Besides the so-called Q enzymes, which introduce branchings into starch molecules, enzymes occur in plants which are capable of breaking down branchings. These enzymes are called debranching enzymes and, according to their substrate specificity, they are divided into three groups:

(a) The pullulanases, which, in addition to pullulan, also utilize amylopectin as substrate, are found in microorganisms, for example *Klebsiella* and in plants. In plants, these enzymes are also termed R enzymes.

(b) The isoamylases, which do not utilize pullulan, but indeed glycogen and amylopectin as substrate, are also found in microorganisms and plants. For example, isoamylases have been described in maize (Manners & Carbohydr. Res. 9 (1969), 107) and potato (Ishizaki et al., Agric. Biol. Chem. 47 (1983), 771–779).

(c) The amylo-1,6-glucosidases are described in mammals and yeasts and utilize grenzdextrins as substrate.

In sugar beet, Li et al. (Plant Physiol. 98 (1992), 1277–1284) were only able to find one debranching enzyme of the pullulanase type, in addition to five endoamylases and two exoamylases. This enzyme, which has a size of approx. 100 kD and a pH optimum of 5.5, is localized in the chloroplasts. In spinach, too, a debranching enzyme was described which utilizes pullulan as substrate. The activity both of the spinach debranching enzyme and of the sugar beet debranching enzyme upon reaction with amylopectin as substrate is five times lower in comparison with pullulan as substrate (Ludwig et al., Plant Physiol. 74 (1984), 856–861; Li et al., Plant Physiol. 98 (1992), 1277–1284).

In the agronomically important starch-storing crop plant potato, the activity of a debranching enzyme was studied by Hobson et al. (J. Chem. Soc., (1951), 1451). It was proved successfully that, in contrast to the 0 enzyme, this enzyme has no chain-extending activity, but merely hydrolyzes alpha-1,6-glycosidic bonds. However, it has been impossible as yet to characterize the enzyme in greater detail. In the case of potatoes, processes for purifying the debranching enzyme and partial peptide sequences of the purified protein have already been proposed (WO 95/04826). In the case of spinach, the purification of a debranching enzyme and the isolation of suitable cDNA have been described in the meantime (Renz et al., Plant Physiol. 108 (1995), 1342).

In maize, only the existence of one debranching enzyme has been described as yet in the literature. Owing to its substrate specificity, this enzyme is classified as belonging to the group of the isoamylases (see, for example, Hannah et al., Scientia Horticulturae 55 (1993), 177–197 or Garwood (1994) in Starch Chemistry and Technology, Whistler, R. L., BeMiller, J. N., Puschall, E. F. (eds.), Academic Press San Diego, New York, Boston, 25–86). The corresponding mutant is termed "sugary". The gene of the sugary locus has been cloned recently (see James et al., Plant Cell 7 (1995), 417–429). Apart from the sugary locus, no other gene locus which encodes a protein with debranching enzyme activity is as yet known in maize. Also, there have been no indications to date that other debranching enzyme forms occur in maize. If transgenic maize plants are to be generated which no longer have any debranching enzyme activities whatsoever, for example in order to extend the degree of branching of the amylopectin starch, it is necessary to identify all debranching enzymes forms which occur in maize and to isolate the corresponding genes or cDNA sequences.

To provide further possibilities of altering any starch-storing plant, preferably cereals, in particular wheat, so that it synthesizes a modified starch, it is necessary to identify in each case DNA sequences which encode further isoforms of branching enzymes.

OBJECTS AND SUMMARY OF THE INVENTION

The object of the present invention is therefore to provide nucleic acid molecules encoding enzymes involved in starch synthesis, which allow genetically modified plants to be generated which make possible the production of plant starches whose chemical and/or physical characteristics are altered.

This object is achieved by providing the use forms designated in the patent claims.

The present invention therefore relates to a nucleic acid molecule which encodes a protein with the function of a wheat isoamylase, preferably a protein which is essentially defined by the amino acid sequence stated under Seq ID No. 3 or 7. In particular, the invention relates to a nucleic acid molecule comprising the nucleotide sequence stated under Seq ID No. 1, 2 or 6, or a part thereof, preferably a molecule comprising the coding region stated in Seq ID No. 1, 2 or 6, and corresponding ribonucleotide sequences. Very especially preferred is a nucleic acid molecule furthermore comprising regulatory elements which ensure transcription and, if appropriate, translation of said nucleic acid molecules. The subject matter of the invention is furthermore a nucleic acid molecule which hybridizes with one of the nucleic acid molecules according to the invention.

The subject matter of the invention is also a nucleic acid molecule encoding a wheat isoamylase whose sequence deviates from the nucleotide sequences of the above-described molecules owing to the degeneracy of the genetic code.

The invention also relates to a nucleic acid molecule with a sequence which is complementary to all or part of one of the abovementioned sequences.

DETAILED DESCRIPTION

The term "hybridization" as used in the context of the present invention denotes hybridization under conventional hybridization conditions, preferably under stringent conditions, as they are described, for example, by Sambrook et al., Molecular Cloning, A Laboratory Manual, 2nd Ed. (1989) Cold Spring Harbor Laboratory Press, Cold Spring Harbor, N.Y.).

"Hybridization" especially preferably takes place under the following conditions:
Hybridization buffer: 2×SSC; 10× Denhardt solution (Fikoll 400+PEG+BSA; ratio 1:1:1); 0.1% SDS; 5 mM EDTA; 50 mM $Na_2HPO_4$; 250 µg/ml Herring sperm DNA; 50 µg/ml tRNA; or 0.25 M sodium phosphate buffer pH 7.2; 1 mM EDTA; 7% SDS
Hybridization temperature T=65 to 70° C.
Wash buffer: 0.2×SSC; 0.1% SDS
Wash temperature T=40 to 75° C.

Nucleic acid molecules which hybridize with the nucleic acid molecules according to the invention are capable, in principle, of encoding isoamylases from any wheat plant which expresses such proteins.

Nucleic acid molecules which hybridize with the molecules according to the invention can be isolated for example from genomic libraries or cDNA libraries of wheat or wheat plant tissue. Alternatively, they can be generated by recombinant methods or synthesized chemically.

Identification and isolation of such nucleic acid molecules can be effected using the molecules according to the invention or parts of these molecules or the reverse complements of these molecules, for example by means of hybridization by standard methods (see, for example, Sambrook et al., 1989, Molecular Cloning, A Laboratory Manual, 2nd Ed. Cold Spring Harbor Laboratory Press, Cold Spring Harbor, N.Y.).

Hybridization probes which can be used are, for example, nucleic acid molecules which have exactly ore essentially the nucleotide sequence stated under SEQ ID NOs:1, 2 or 6 or parts of these sequences. The fragments used as hybridization probes may also be synthetic fragments which have been prepared with the aid of the customary synthetic techniques whose sequence essentially agrees with that of a nucleic acid molecule according to the invention.

The molecules hybridizing with the nucleic acid molecules according to the invention also encompass fragments, derivatives and allelic variants of the above-described nucleic acid molecules which encode a wheat isoamylase according to the invention. Fragments are to be understood as meaning parts of the nucleic acid molecules of sufficient length so as to encode one of the proteins described. The term derivative means in this context that the sequences of these molecules differ from the sequences of the above-described nucleic acid molecules at one or more positions and have a high degree of homology with these sequences. Homology means a sequence identity of at least 40%, in particular of at least 60%, preferably over 80%, especially preferably over 90%. The deviations relative to the above-described nucleic acid molecules may have been generated by deletion, substitution, insertion or recombination.

Homology furthermore means that functional and/or structural equivalence exists between the nucleic acid molecules in question or the proteins encoded by them. The nucleic acid molecules which are homologous to the above-described molecules and constitute derivatives of these molecules are, as a rule, variations of these molecules which constitute modifications exerting the same biological function. They may be naturally occurring variations, for example, sequences from other organisms, or mutations which may have occurred naturally or been introduced by directed mutagenesis. Furthermore, the variations may be synthetically generated sequences. The allelic variants may be both naturally occurring variants and synthetically generated variants or variants produced by recombinant DNA techniques.

The isoamylases encoded by the various variants of the nucleic acid molecules according to the invention share certain characteristics. These may include, for example, enzyme activity, molecular weight, immunological reactivity, conformation and the like, or else physical properties such as, for example, the migration behavior in gelelectrophoresis, the chromatographic behavior, sedimentation coefficients, solubility, spectroscopic characteristics, charge characteristics, stability; pH optimum, temperature optimum and the like.

The protein encoded by the nucleic acid molecules according to the invention is a wheat isoamylase. These proteins show certain homology ranges with isoamylases from other plant species which are already known.

The nucleic acid molecules according to the invention may be DNA molecules, in particular cDNA or genomic molecules. Furthermore, the nucleic acid molecules according to the invention may be RNA molecules which may result, for example, from the transcription of a nucleic acid molecule according to the invention. The nucleic acid molecules according to the invention may have been obtained, for example, from natural sources or they may have been generated by recombinant techniques or synthesized.

Subject matter of the invention are also oligonucleotides which hybridize specifically with a nucleic acid molecule according to the invention. Such oligonucleotides preferably have a length of at least 10, in particular of at least 15 and especially preferably of at least 50 nucleotides. The oligonucleotides according to the invention hybridize specifically with nucleic acid molecules according to the invention, i.e. not or only to a very low degree with nucleic acid sequences which encode other proteins, in particular other isoamylases. The oligonucleotides according to the invention can be used, for example, as primers for a PCR reaction or as hybridization probe for the isolation of the related genes. Equally, they may be constituents of antisense constructs or of DNA molecules encoding suitable ribozymes.

The invention furthermore relates to vectors, in particular plasmids, cosmids, phagemids, viruses, bacteriophages and other vectors conventionally used in genetic engineering comprising the above-described nucleic acid molecules according to the invention. Such vectors are suitable for the transformation of pro- or eukaryotic cells, preferably plant cells.

The vectors especially preferably permit integration of the nucleic acid molecules according to the invention, if appropriate together with flanking regulatory regions, into the genome of the plant cell. Examples are binary vectors which can be employed in agrobacterial-mediated gene transfer. Preferably, integration of a nucleic acid molecule according to the invention in sense or antisense orientation ensures that a translatable or, if appropriate, nontranslatable RNA is synthesized in the transformed pro- or eukaryotic cells.

The term "vector" generally denotes a suitable auxiliary known to the skilled worker which allows the directed transfer of a single- or double-stranded nucleic acid molecule into a host cell, for example a DNA or RNA virus, a virus fragment, a plasmid construct which, in the absence or presence of regulatory elements, may be suitable for transferring nucleic acid into cells, or support materials such as glass fibers or else metal particles as can be employed, for example, in the particle gun method, but it may also encompass a nucleic acid molecule which can be introduced directly into a cell by means of chemical or physical methods.

In a preferred embodiment, the nucleic acid molecules within the vectors are linked to regulatory elements which ensure transcription and synthesis of a translatable RNA in pro- or eukaryotic cells or which—if desired—ensure synthesis of a nontranslatable RNA.

Expression of the nucleic acid molecules according to the invention in prokaryotic cells, for example, in *Escherichia coli*, is of importance for a more detailed characterization of the enzymatic activities of the enzymes encoded by these molecules. In particular, it is possible to characterize the product synthesized by the enzymes in question in the absence of other enzymes involved in starch synthesis in the plant cell. This permits conclusions to be drawn regarding the function which the protein in question exerts during starch synthesis in the plant cell.

In addition, various types of mutations can be introduced into the nucleic acid molecules according to the invention by means of customary techniques of molecular biology (see, for example, Sambrook et al., 1989, Molecular Cloning, A Laboratory Manual, 2nd Ed. Cold Spring Harbor Laboratory Press, Cold Spring Harbor, N.Y.), resulting in the synthesis of proteins whose biological properties may be altered. Possible here is, on the one hand, the generation of deletion mutants in which nucleic acid molecules are generated by successive deletions from the 5' or the 3' end of the coding DNA sequence which lead to the synthesis of correspondingly truncated proteins. Such deletions at the 5' end of the nucleotide sequence allow, for example, amino acid sequences to be identified which are responsible for translocation of the enzyme into the plastids (transit peptides). This allows the directed generation of enzymes which, owing to the removal of the sequences in question, are no longer localized in the plastids, but in the cytosol, or which, owing to the addition of other signal sequences, are localized in other compartments.

On the other hand, it is also possible to introduce point mutations at positions where an altered amino acid sequence affects, for example, enzyme activity or enzyme regulation. In this manner, it is possible to generate, for example, mutants which have an altered $K_m$ value or which are no longer subject to the regulatory mechanisms via allosteric regulation or covalent modification which are normally present in the cell.

Furthermore, it is possible to generate mutants which have an altered substrate or product specificity of the protein according to the invention. Furthermore, it is possible to generate mutants which have an altered activity-temperature profile of the protein according to the invention.

To carry out the recombinant modification of prokaryotic cells, the nucleic acid molecules according to the invention or parts of these molecules can be introduced into plasmids which allow mutagenesis to take place or a sequence to be altered by recombining DNA sequences. Base exchanges can be carried out or natural or synthetic sequences added with the aid of standard methods (cf. Sambrook et al., 1989, Molecular Cloning: A laboratory manual, 2nd Ed., Cold Spring Harbor Laboratory Press, NY, USA). To link the DNA fragments to each other, adapters or linkers may be attached to the fragments. Furthermore, manipulations may be employed which provide suitable restriction cleavage sites or which eliminate superfluous DNA or restriction cleavage sites. Where insertions, deletions or substitutions are suitable, in vitro mutagenesis, primer repair, restriction or ligation may be employed. Analytical methods which are generally employed are sequence analysis, restriction analysis or other methods of biochemistry and molecular biology.

In a further embodiment, the invention relates to host cells, in particular pro- or eukaryotic cells, which have been transformed with an above-described nucleic acid molecule according to the invention or a vector according to the invention, and to cells which are derived from cells transformed thus and comprise a nucleic acid molecule according to the invention or a vector. They are preferably pro- or eukaryotic cells, in particular plant cells.

Subject matter of the invention are furthermore proteins with isoamylase activity which are encoded by the nucleic acid molecules according to the invention and which can be prepared by recombinant technology, and processes for their preparation, where a host cell according to the invention is cultured under suitable conditions which are known to the skilled worker and which permit synthesis of the protein according to the invention and it is subsequently isolated from the host cells and/or the culture medium.

Providing the nucleic acid molecules according to the invention now makes it possible to intervene, with the aid of recombinant methods, in a directed fashion in the starch metabolism of plants and to alter it so that the resultant synthesis is of modified starch whose physicochemical properties, for example the amylose/amylopectin ratio, the degree of branching, the average chain length, the phosphate content, the gelatinization behavior, the gel- or film-forming properties, the starch granule size and/or the starch granule shape is altered in comparison to known starch.

Thus, it is possible to express the nucleic acid molecules according to the invention in plant cells in order to increase the activity of the isoamylase in question, or to introduce them into cells which do not naturally express this enzyme. Expressing the nucleic acid molecules according to the invention also makes it possible to lower the natural activity level of the isoamylase according to the invention in the plant cells. Furthermore, it is possible to modify the nucleic acid molecules according to the invention by methods known to the skilled worker in order to obtain isoamylases according to the invention which are no longer subject to the cell's intrinsic regulatory mechanism or which have altered temperature-activity profiles or substrate or product specificities.

When expressing the nucleic acid molecules according to the invention in plants, it is possible, in principle, for the protein synthesized to be localized in any desired compartment of the plant cell. To achieve localization in a particular compartment, the sequence ensuring localization in plastids must be deleted and the remaining encoding region must, if necessary, be linked to DNA sequences which ensure localization in the compartment in question. Such sequences are known (see, for example, Braun et al., EMBO J. 11 (1992), 3219–3227; Wolter et al., Proc. Natl., Acad. Sci. USA 85 (1988), 846–850; Sonnewald et al., Plant J. 1 (1991), 95–106).

The present invention thus also relates to a method for generating transgenic plant cells which have been transformed with a nucleic acid molecule or a vector according to the invention, where a nucleic acid molecule according to the invention or a vector according to the invention is integrated into the genome of a plant cell, the transgenic plant cells which have been transformed by means of a vector or nucleic acid molecule according to the invention, and transgenic plant cells derived from cells transformed thus. The cells according to the invention comprise one or more nucleic acid molecules or vectors according to the invention, these preferably being linked to regulatory DNA elements which ensure transcription in plant cells, in particular to a suitable promoter. Such cells can be distinguished from naturally occurring plant cells inter alia by the fact that they comprise a nucleic acid molecule according to the invention which does not occur naturally in these cells, or by the fact that such a molecule exists integrated at a location in the cell's genome where it does not occur otherwise, i.e. in a different genomic environment. Furthermore, such transgenic plant cells according to the invention can be distinguished from naturally occurring plant cells by the fact that they comprise at least one copy of a nucleic acid molecule according to the invention stably integrated into the genome, if appropriate in addition to the copies of such a molecule which occur naturally in the cells. If the nucleic acid molecule(s) introduce into the cells is(are) additional copies to molecules which already occur naturally in the cells, then the plant cells according to the invention can be distinguished from naturally occurring plant cells in particular by the fact that this additional copy, or these additional copies, is, or are, localized at locations in the genome where it does not occur naturally, or they do not occur naturally. This can be checked, for example, with the aid of a Southern blot analysis.

If the nucleic acid molecule according to the invention which has been introduced into the plant genome is heterologous to the plant cell, the transgenic plant cells exhibit transcripts of the nucleic acid molecules according to the invention which can be detected in a simple manner by methods known to the skilled worker, for example by Northern blot analysis.

If the nucleic acid molecule according to the invention which has been introduced is homologous to the plant cell, the cells according to the invention can be distinguished from naturally occurring cells, for example, on the basis of the additional expression of nucleic acid molecules according to the invention. The transgenic plant cells preferably comprise more transcripts of the nucleic acid molecules according to the invention. This can be detected, for example, by Northern blot analysis. "More" in this context means preferably at least 10% more, preferably at least 20% more, especially preferably at least 50% more transcripts than corresponding untransformed cells. The cells furthermore preferably exhibit a corresponding increase or decrease in the activity of the protein according to the invention (at least 10%, 20% or 50%). The transgenic plant cells can be regenerated into intact plants by techniques known to the skilled worker.

Another subject matter of the present invention is a method for the generation of transgenic plants, where one or more nucleic acid molecules or vectors according to the invention are integrated into the genome of a plant cell and a complete plant is regenerated from said plant cell. Subject matter of the invention are furthermore plants which comprise the above-described transgenic plant cells. In principle, the transgenic plants can be plants of any species, i.e. not only monocotyledonous but also dicotyledonous plants. They are preferably useful plants, by preference starch-synthesizing or starch-storing plants, especially preferably rye, barley oats, wheat, sorghum and millet, sago, maize, rice, peas, marrowfat peas, cassava, potatoes, tomatoes, oilseed rape, soybeans, hemp, flax, sunflowers, cowpeas or arrowroot, in particular wheat, maize, rice and potatoes.

The invention also relates to propagation material of the plants according to the invention, for example fruits, seeds, tubers, rootstocks, seedlings, cuttings, calli, protoplasts, cell cultures and the like.

The present invention furthermore relates to a process for the preparation of a modified starch comprising the step of extracting the starch from an above-described plant according to the invention and/or starch-storing parts of such a plant.

Processes for extracting the starch from plants or starch-storing parts of plants, in particular from wheat, are known to the skilled worker, cf., for example, Eckhoff et al. (Cereal Chem. 73 (1996) 54–57) "Starch: Chemistry and Technology (Eds.: Whistler, BeMiller and Paschall (1994), 2nd Edition, Academic Press Inc. London Ltd; ISBN 0-12-746270-8; see, for example, Chapter XII, pages 412–468: Corn and sorghum starches: production; by Watson; Chapter XIII, pages 469–479; Tapioca, arrowroot and sago starches: production; by Corbishley and Miller; Chapter XIV, pages 479–490: Potato starch: production and uses; by Mitch; Chapter XV, pages 491 to 506: Wheat starch: production, modification and uses; by Knight and Oson; and Chapter XVI, pages 507 to 528: Rice starch: production and uses; by Rohmer and Klem). Devices normally used in processes for extracting starch from plant material are separators, decanters, hydrocyclones, spray dryers and fluidized-bed dryers.

Owing to the expression of a nucleic acid molecule according to the invention, the transgenic plant cells and plants according to the invention synthesize a starch whose physicochemical properties, for example the amylose/amylopectin ratio, the degree of branching, the average chain length, the phosphate content, the gelatinization behavior, the starch granule size and/or starch granule shape is altered compared with starch synthesized in wild-type plants. In particular, such a starch may be altered with regard to viscosity and/or the film- or gel-forming properties of gels made from this starch in comparison with known starches.

Subject matter of the present invention is furthermore a starch which is obtainable from the plant cells and plants according to the invention and their propagation material and starch which is obtainable by the above-described process according to the invention.

It is furthermore possible to generate, with the aid of the nucleic acid molecules according to the invention, plant cells and plants in which the activity of a protein according to the invention is reduced. This also leads to the synthesis of a starch with altered chemical and/or physical characteristics compared with starch from wild-type plant cells.

A further subject matter of the invention is thus also a transgenic plant cell comprising a nucleic acid molecule according to the invention in which the activity of an isoamylase is reduced in comparison with untransformed cells.

Plant cells with a reduced activity of an isoamylase can be obtained, for example, by expressing a suitable antisense RNA, a sense RNA for achieving a cosuppression effect or by expressing a suitably constructed ribozyme which specifically cleaves transcripts which encode an isoamylase, making use of the nucleic acid molecules according to the invention by methods known to the skilled worker, cf. Jorgensen (Trends Biotechnol. 8 (1990), 340–344), Niebel et al., (Curr. Top. Microbiol. Immunol. 197 (1995), 91–103), Flavell et al. (Curr. Top. Microbiol. Immunol 197 (1995), 43–46), Palaqui and Vaucheret (Plant. Mol. Biol. 29 (1995), 149–159), Vaucheret et al., (Mol. Gen. Genet. 248 (1995), 311–317), de Borne et al. (Mol. Gen. Genet. 243 (1994), 613–621).

To reduce the activity of an isoamylase according to the invention, it is preferred to reduce, in the plant cells, the number of transcripts encoding it, for example by expressing an antisense RNA.

Here, it is possible to make use, on the one hand, of a DNA molecule which encompasses all of the sequence encoding a protein according to the invention, inclusive of any flanking sequences which may be present, or else of DNA molecules which only encompass parts of the coding sequence, it being necessary for these parts to be sufficiently long so as to cause an antisense effect in the cells. In general, sequences up to a minimum length of 15 bp, preferably with a length of 100–500 bp, may be used for efficient antisense inhibition in particular sequences with a length of over 500 bp. As a rule, DNA molecules are used which are shorter than 5000 bp, preferably sequences which are shorter than 2500 bp.

Also possible is the use of DNA sequences which show a high degree of homology with the sequences of the DNA molecules according to the invention, but are not completely identical. The minimum homology should exceed approx. 65%. The use of sequences with homologies between 95 and 100% is to be preferred.

Subject matter of the invention is also a process for producing a modified starch encompassing the step of extracting the starch from a cell or plant according to the invention and/or from starch-storing parts of such a plant.

Subject matter of the invention is furthermore starch which can be obtained from the cells or plants according to the invention and their propagation material or parts, and also starch which can be obtained by a process according to the invention.

The starches according to the invention can be modified by methods known to the skilled worker and are suitable, in their unmodified or modified form, for a variety of applications in the food or non-food sectors.

In principle, the possible uses of the starches according to the invention can be divided into two important sectors. One sector encompasses the hydrolyzates of the starch, mainly glucose and glucan units, which are obtained by enzymatic or chemical methods. They are used as starting material for further chemical modifications and processes such as fermentation. What would be feasible for reducing the costs is the simplicity and economic design of a hydrolytic method. It currently proceeds essentially enzymatically using amyloglucosidase. What would be feasible is a financial saving by using less enzyme. This could be caused by altering the structure of the starch, for example by increasing the surface area of the granule, better digestibility, for example owing to a lower degree of branching or a sterical structure which limits the accessibility for the enzymes employed.

The other sector in which the starch according to the invention can be used as so-called native starch, owing to its polymeric structure, can be divided into two further fields of application:

1. The Food Industry
    Starch is a traditional additive to a large number of foodstuffs in which its function is essentially to bind aqueous additives or to cause increased viscosity or else increased gelling. Important characteristics are the rheology, the sorptive characteristics, the swelling temperature, the gelatinization temperature, the viscosity, the thickening power, the starch solubility, the transparency and gel structure, the thermal stability, the shear stability, the stability to acids, the tendency to undergo retrogradation, the film-forming capacity, the freeze-thaw stability, the viscosity stability in salt solutions, the digestibility and the ability to form complexes with, for example, inorganic or organic ions.

2. The Non-food Industry
    In this large sector, starch can be employed as auxiliary for various preparation processes or as an additive in industrial products. When using starch as an auxiliary, mention must be made, in particular, of the paper and board industry. Starch acts mainly for retardation purposes (retaining solids), for binding filler particles and fines, as stiffener and for dehydration. Moreover, the advantageous properties of starch regarding stiffness, strength, sound, touch, luster, smoothness, bonding strength and the surfaces is utilized.

2.1 Paper and Board Industry

Within the papermaking process, four fields of application must be distinguished, i.e. surface, coating, stock and spraying. The demands on starch with regard to surface treatment are essentially high whiteness, an adapted viscosity, high viscosity stability, good film formation and low dust formation. When used for coating, the solids content, a suitable viscosity, a high binding capacity and a high pigment affinity play an important role. Of importance when used as additive to the stock is rapid, uniform, loss-free distribution, high mechanical strength and complete retention in the paper web. If the starch is used in the spraying sector, again, an adapted solids content, high viscosity and high binding capacity are of importance.

2.2 The Adhesives Industry

An important field of application for starches is the adhesives industry, where the potential uses can be divided into four subsections: the use as a pure starch paste, the use in starch pastes which have been treated with specialty chemicals, the use of starch as additive to synthetic resins and polymer dispersions, and the use of starches as extenders for synthetic adhesives. 90% of the starch-based adhesives are employed in the sectors production of corrugated board, production of paper sacks and bags, production of composite materials for paper and aluminum, production of boxes and gumming adhesives for envelopes, stamps and the like.

2.3 Textile Industry and Textile Care Products Industry

An important field of application for starches as auxiliaries and additives is the sector production of textiles and textile care products. The following four fields of application must be distinguished within the textile industry: the use of starch as sizing agent, i.e. as auxiliary for smoothing and strengthening the smoothing behavior as protection from the tensile forces applied during weaving, and for increasing abrasion resistance during weaving, starch as a textile finishing agent, in particular after quality-reducing pretreatments such as bleaching, dyeing and the like, starch as thickener in the preparation of dye pastes for preventing bleeding, and starch as additive to glazing agents for sewing threads.

2.4 Construction Materials Industry

The fourth field of application is the use of starches as additives in construction materials. An example is the production of gypsum plasterboards, where the starch which is admixed to the gypsum slurry gelatinizes with the water, diffuses to the surface of the plaster core and there binds the board to the core. Other fields of application are the admixture to rendering and mineral fibers. In the case of ready-mixed concrete, starch products are employed for delaying binding.

2.5 Soil Stabilization

Another market for starch products is the production of soil stabilizers, which are employed for the temporary protection of the soil particles from water when the soil is disturbed artificially. According to present knowledge, product combinations of starch and polymer emulsions equal the previously employed products with regard to their erosion- and crust-reducing effect, but are markedly less expensive.

2.6 Use in Crop Protection Products and Fertilizers

One field of application for using starch is in crop protection products for altering the specific properties of the products. Thus, starch can be employed for improving the wettability of crop protection products and fertilizers, for the controlled release of the active ingredients, for converting liquid, volatile and/or malodorous active ingredients into microcrystalline, stable, shapeable substances, for mixing incompatible compounds and for extending the duration of action by reducing decomposition.

2.7 Pharmaceuticals, Medicine and Cosmetics Industry

Another field of application is the sector of the pharmaceuticals, medicine and cosmetics industry. In the pharmaceuticals industry, starch can be employed as binder for tablets or for diluting the binder in capsules. Moreover, starch can be employed as tablet disintegrant since it absorbs fluid after swallowing and swells within a short time to such an extent that the active ingredient is liberated. Medicinal lubricating powders and wound powders are starch-based for reasons of quality. In the cosmetics sector, starches are employed, for example, as carriers of powder additives such as fragrances and salicylic acid. A relatively large field of application for starch is toothpaste.

2.8 Addition of Starch to Coal and Briquettes

A field of application for starch is as additive to coal and briquettes. With an addition of starch, coal can be agglomerated, or briquetted, in terms of high quantity, thus preventing premature decomposition of the briquettes. In case of barbecue coal, the starch addition amounts to between 4 and 6%, in the case of calorized coal to between 0.1 and 0.5%. Moreover, starches are gaining importance as binders since the emission of noxious substances can be markedly reduced when starches are added to coal and briquettes.

2.9 Ore Slick and Coal Silt Processing

Furthermore, starch can be employed as flocculant in the ore slick and coal silt processing sector.

2.10 Foundry Auxiliary

A further field of application is as additive to foundry auxiliaries. Various casting processes require cores made with sands treated with binders. The binder which is predominantly employed nowadays is bentonite, which is treated with modified starches, in most cases swellable starches.

The purpose of adding starch is to increase flowability and to improve the binding power. In addition, the swellable starches can meet other demands of production engineering, such as being cold-water-dispersible, rehydratable, readily miscible with sand and having high water-binding capacity.

2.11 Use in the Rubber Industry

In the rubber industry, starch is employed for improving the technical and visual quality. The reasons are the improvement of the surface luster, the improvement of handle and of appearance, and to this end starch is scattered on to the tacky gummed surface of rubber materials prior to cold curing, and also the improvement of the rubber's printability.

2.12 Production of Leather Substitutes

Modified starches may furthermore also be sold for the production of leather substitutes.

2.13 Starch in Synthetic Polymers

In the polymer sector, the following fields of application can be envisaged: the use of starch degradation products in the processing process (starch only acts as filler, there is no direct bond between the synthetic polymer and the starch) or, alternatively, the use of starch degradation products in the production of polymers (starch and polymer form a stable bond).

The use of starch as a pure filler is not competitive in comparison with other substances such as talc. However, this is different when the specific properties of starch make an impact and thus markedly alter the spectrum of characteristics of the end products. An example of this is the use of starch products in the processing of thermoplastics, such as polyethylene. Here, the starch and the synthetic polymer are combined by coexpression in a ratio of 1:1 to give a master batch, from which various products are produced with granulated polyethylene, using conventional process techniques. By using starch in polyethylene films, an increased substance permeability in the case of hollow bodies, an improved permeability for water vapor, an improved antistatic behavior, an improved antiblock behavior and an improved printability with aqueous inks can be achieved.

Another possibility is the use of starch in polyurethane foams. By adapting the starch derivatives and by process-engineering optimization, it is possible to control the reaction between synthetic polymers and the starches' hydroxyl groups in a directed manner. This results in polyurethane films which have the following spectrum of properties, owing to the use of starch: a reduced heat expansion coefficient, a reduced shrinking behavior, an improved pressure-tension behavior, an increase in permeability for water vapor without altering the uptake of water, a reduced flammability and a reduced ultimate tensile strength, no drop formation of combustible parts, freedom from halogens, or else reduced aging. Disadvantages which still exist are reduced printability and reduced impact strength.

Product development is currently no longer restricted to films. Solid polymer products such as pots, slabs and dishes which have a starch content of over 50% may also be produced. Moreover, starch/polymer mixtures are considered advantageous since their biodegradability is much higher.

Starch graft polymers have become exceedingly important owing to their extremely high water binding capacity. They are products with a starch backbone and a side lattice of a synthetic monomer, grafted on following the principle of the free-radical chain mechanism. The starch graft polymers which are currently available are distinguished by a better binding and retention capacity of up to 1000 g of water per g of starch combined with high viscosity. The fields of application of these superabsorbers have extended greatly in recent years and are, in the hygiene sector, products such as diapers and pads and, in the agricultural sector, for example seed coatings.

What is decisive for the application of novel, genetically modified starches are, on the one hand, structure, water content, protein content, lipid content, fiber content, ash/phosphate content, amylose/amylopectin ratio, molecular mass distribution, degree of branching, granule size and granule shape and crystallinity, and, on the other hand, also the characteristics which effect the following features: flow and sorption behavior, gelatinization temperature, viscosity, viscosity stability in salt solutions, thickening power, solubility power, gel structure and gel transparency, thermal stability, shear stability, stability to acids, tendency to undergo retrogradation, gel formation, freeze-thaw stability, complex formation, iodine binding, film formation, adhesive power, enzyme stability, digestibility and reactivity.

The production of modified starches by recombinant methods can, on the one hand, alter the properties of the starch derived from the plant in such a way that other modifications by means of chemical or physical processes are no longer required. On the other hand, starches which have been altered by recombinant methods may be subjected to further chemical modification, which leads to further improvements in quality for some of the above-described fields of application. These chemical modifications are known in principle. They are, in particular, modifications by thermal treatment, treatment with organic or inorganic acids, oxidation and esterifications, which lead, for example, to the formation of phosphate starches, nitrate starches, sulfate starches, xanthate starches, acetate starches and citrate starches. Moreover, mono- or polyhydric alcohols in the presence of strong acids may be employed for producing starch ethers, resulting in starch alkyl ethers, O-allyl ethers, hydroxyalkyl ethers, O-carboxy methyl ethers, N-containing starch ethers, P-containing starch ethers), S-containing starch ethers, crosslinked starches or starch graft polymers.

A preferred use of the starches according to the invention is the production of packaging materials and disposable articles, on the one hand, and as foodstuff or foodstuff precursor on the other hand.

To express the nucleic acid molecules according to the invention in sense or antisense orientation in plant cells, they are linked to regulatory DNA elements which ensure transcription in plant cells. These include, in particular, promoters, enhancers and terminators. In general, any promoter which is active in plant cells is suitable for expression.

The promoter may be chosen in such a way that expression is constitutive or takes place only in a particular tissue, at a particular point in time of plant development or at a point in time determined by external factors. Relative to the plant, the promoter can be homologous or heterologous. Examples of suitable promoters are the cauliflower mosaic virus 35S RNA promoter and the maize ubiquitin promoter for constitutive expression, the patatin promoter B33 (Rocha-Sosa et al., EMBO J. 8 (1989), 23–29) for tuber-specific expression, or a promoter which ensures expression only in photosynthetically active tissue, for example the ST-LS1 promoter (Stockhaus et al., Proc. Natl. Acad. Sci. USA 84 (1987), 7943–7947; Stockhaus et al., EMBO J. 8 (1989), 2445–2451) or, for endosperm-specific expression, the wheat AMG promoter, the USP promoter, the phaseolin promoter or promoters from maize zein genes.

A termination sequence which serves to correctly terminate transcription and to add a poly-A tail to the transcript, which is considered to have a function in stabilizing the transcripts, may also be present. Such elements have been described in the literature (cf. Gielen et al., EMBO J. 8 (1989), 23–29) and are exchangeable as desired.

The present invention provides nucleic acid molecules which encode a protein with a wheat isoamylase function. The nucleic acid molecules according to the invention permit the production of this enzyme whose functional identification in starch biosynthesis, the generation of plants which have been altered by recombinant technology in which the activity of this enzyme is altered and thus allows a starch to be synthesized in plants modified thus whose structure is altered and whose physicochemical properties are altered.

In principle, the nucleic acid molecules according to the invention may also be used for generating plants in which the activity of the isoamylase according to the invention is increased or reduced while simultaneously the activities of other enzymes which participate in starch synthesis are altered. Altering the activities of an isoamylase in plants results in the synthesis of a starch with altered structure.

Furthermore, nucleic acid molecules which encode an isoamylase or suitable antisense constructs can be introduced into plant cells in which the synthesis of endogenous starch synthases or branching enzymes is already inhibited (as, for example, in WO 92/14827 or Shannon and Garwood, 1984, in Whistler, BeMiller and Paschall, Starch: Chemistry and Technology, Academic Press, London, 2nd Edition: 25–86).

If it is intended to achieve the inhibition of the synthesis of several enzymes involved in starch biosynthesis in transformed plants, the transformation may involve DNA molecules which simultaneously comprise several regions encoding the enzymes in question in antisense orientation under the control of a suitable promoter. Here, it is possible for each sequence to be under the control of its own promoter, or for the sequences to be transcribed by a joint promoter as a fusion or to be under the control of a joint promoter. The last-mentioned alternative will generally be preferred, since in this case the synthesis of the proteins in question should be inhibited roughly to the same extent. As regards the length of the individual coding regions used in such a construct, what has been mentioned above for the generation of antisense constructs also applies here. In principle, there is no upper limit for the number of antisense fragments to transcribed in such a DNA molecule starting from one promoter. However, the transcript formed should preferably not exceed a length of 10 kb, in particular a length of 5 kb.

Coding regions localized in such DNA molecules in combination with other coding regions in antisense orientation behind a suitable promoter may be derived from DNA sequences which encode the following proteins: starch-granule-bound starch synthases (GBSS I and II) and soluble starch synthases (SSS I and II), branching enzymes (isoamylases, pullulanases, R enzymes, branching enzymes, debranching enzymes), starch phosphorylases and disproportioning enzymes. This enumeration is only by way of example The use of other DNA sequences for the purposes of such a combination is also feasible.

Such constructs allow the synthesis of a plurality of enzymes to be inhibited simultaneously in plant cells transformed with them.

Furthermore, the constructs can be introduced into plant mutants which are deficient for one or more starch biosynthesis genes (Shannon and Garwood, 1984, in Whistler, BeMiller and Paschall, Starch: Chemistry and Technology, Academic Press, London, 2nd Edition: 25–86). These defects may relate to the following proteins: starch-granule-bound starch synthases (GBSS I and II) and soluble starch synthases (SSS I and II), branching enzymes (BE I and II), debranching enzymes (R enzymes), disproportioning enzymes and starch phosphorylases. This enumeration is only by way of example.

Such a procedure furthermore allows the synthesis of a plurality of enzymes to be inhibited simultaneously in plant cells transformed with them.

To prepare the introduction of foreign genes into higher plants, a large number of cloning vectors containing a replication signal for $E.coli$ and a marker gene for selecting transformed bacterial cells is available. Examples of such vectors are pBR322, pUC series, M13mp series, pACYC184 and the like. The desired sequence may be introduced into the vector at a suitable restriction cleavage site. The plasmid obtained is used to transform $E.coli$ cells. Transformed $E.coli$ cells are grown in a suitable medium and subsequently harvested and lyzed. The plasmid is recovered. Analytical methods for characterizing the plasmid DNA obtained which are generally used are restriction analyses, gel electrophoresis and further methods of biochemistry and molecular biology. After each manipulation, the plasmid DNA can be cleaved and resulting DNA fragments linked to other DNA sequences. Each plasmid DNA sequence can be cloned in identical or different plasmids.

A large number of techniques is available for introducing DNA into a plant host cell. These techniques encompass transformation of plant cells with t-DNA using $Agrobacterium\ tumefaciens$ or $Agrobacterium\ rhizogenes$ as transformation agents, protoplast fusion, injection, the electroporation of DNA, the introduction of DNA by means of the biolistic method, and other possibilities.

The injection and electroporation of DNA into plant cells per se require no particular aspect of the plasmids used. Simple plasmids such as, for example, pUC derivatives may be used. However, if intact plants are to be regenerated from such transformed cells, the presence of a selectable marker gene is generally required.

Depending on the method of introducing desired genes into the plant cell, further DNA sequences may be required. If, for example, the Ti or Ri plasmid is used for transforming the plant cell, at least the right border, but frequently the right and left borders, of the Ti and Ri plasmid T-DNA must be linked to the genes to be introduced as flanking region.

If agrobacteria are used for the transformation, the DNA to be introduced must be cloned into specific plasmids, either into an intermediate vector or into a binary vector. The intermediate vectors can be integrated into the agrobacterial Ti or Ri plasmid by homologous recombination owing to sequences which are homologous to sequences in the T-DNA. The former also contains the vir region, which is required for the T-DNA transfer. Intermediate vectors cannot replicate in agrobacteria. The intermediate vector can be transferred to $Agrobacterium\ tumefaciens$ (conjugation) by means of a helper plasmid. Binary vectors are capable of replication in $E.coli$ and in agrobacteria. They contain a selection marker gene and a linker or polylinker, which are framed by the left and right T-DNA border regions. They can be transformed directly into the agrobacteria (Holsters et al. Mol. Gen. Genet. 163 (1978), 181–187). The $agrobacterium$ which acts as the host cell should contain a plasmid carrying a vir region. The vir region is required for transferring the T-DNA into the plant cell. Additional T-DNA may be present. The $agrobacterium$ thus transformed can be used for transforming plant cells.

The use of T-DNA for transforming plant cells has been researched intensively and been described in EP 120 516; Hoekema, In: The Binary Plant Vector System Offsetdrukkerij Kanters B. V., Alblasserdam (1985), Chapter V; Fraley et al., Crit. Rev. Plant. Sci., 4, 1–46 and An et al. EMBO J. 4 (1985), 277–287.

To transfer the DNA into the plant cell, plant explants can expediently be cocultured with $Agrobacterium\ tumefaciens$ or $Agrobacterium\ rhizogenes$. Intact plants can then be regenerated again from the infected plant material (for example leaf sections, stalk sections, roots, but also protoplasts, or plant cells grown in suspension culture) in a suitable medium which can contain, inter alia, certain sugars, amino acids, antibiotics or biocides for selecting transformed cells. The resulting plants can then be examined for the presence of the DNA which has been introduced. Other possibilities of introducing foreign DNA using the biolistic method or by protoplast transformation are known (cf., for example, Willmitzer, L., 1993 Transgenic plants. In: Biotechnology, A Multi-Volume Comprehensive Treatise (H. J. Rehm, G. Reed, A. Pühler, P. Stadler, eds.), Vol. 2, 627–659, VCH Weinheim-New York-Basel-Cambridge).

While the transformation of the dicotyledonous plants via Ti-plasmid vector systems with the aid of *Agrobacterium tumefaciens* is well established, more recent work suggests that even monocotyledonous plants are indeed accessible to transformation by means of *agrobacterium*-based vectors (Chan et al., Plant Mol. Biol. 22 (1993), 491–506; Hiei et al., Plant J. 6 (1994), 271–282).

Alternative methods for the transformation of monocotyledonous plants are the transformation by means of the biolistic approach, protoplast transformation, or the physically- or chemically-induced DNA uptake into protoplasts, for example by electroporation of partially permeabilized cells, transfer of DNA by means of glass fibers, macroinjection of DNA into inflorescences, the microinjection of DNA into microspores or proembryos, DNA uptake by germinating pollen and DNA uptake in embryos by swelling (review: Potrykus, Physiol. Plant (1990), 269–273).

Three of the abovementioned transformation systems have been established in the past for various cereals: the electroporation of tissue, the transformation of protoplasts and the DNA transfer by particle bombardment into regenerable tissue and cells (review: Jähne et al., Euphytica 85 (1995), 35–44).

Different methods of transforming wheat have been described in the literature (review: Maheshwari et al., Critical Reviews in Plant Science 14 (2) (1995), 149 to 178): Hess et al. (Plant Sci. 72 (1990), 233) employ the macroinjection method to bring pollen and agrobacteria into the immediate vicinity. The mobilization of the plasmid which contained the nptII gene as selectable marker was detected by Southern blot analysis and NPTII test. The transformants showed a normal phenotype and were fertile. Kanamycin resistance was detected in two consecutive generations.

The first transgenic fertile wheat plant which was regenerated after bombardment with DNA bound to microprojectiles was described by Vasil et al. (Bio/Technology 10 (1992), 667–674). The target tissue for the bombardment was an embryogenic callus culture (type C callus). The selection marker employed was the bar gene which encodes a phosphinothricin acetyl transferase and thus mediates resistance to the herbicide phosphinothricin. A further system was described by Weeks et al. (Plant Physiol. 102 (1993), 1077–1084), and Becker et al. (Plant J. 5(2) (1994), 299–307). Here, the target tissue for the DNA transformation is the scutellum of immature embryos which was stimulated in a preliminary in-vitro phase to induce somatic embryos. The transformation efficacy in the system developed by Becker et al. (loc cit.) is 1 transgenic plant per 83 embryos of the variety "Florida" and thus markedly higher than the system established by Weeks et al., which yields 1 to 2 transgenic plants per 1000 embryos of the variety "Bohwhite".

The system developed by Becker et al. (loc Cit) forms the basis for the transformation experiments described in the examples.

Once the DNA introduced is integrated into the genome of the plant cell, it is, as a rule, stable and is also retained in the progeny of the originally transformed cell. It normally contains one of the above-mentioned selection markers which mediates, for example, resistance to a biocide such as phosphinothricin or an antibiotic such as kanamycin, G 418, bleomycin or hygromycin, to the transformed plant cells or which permits selection via the presence or absence of certain sugars or amino acids. The marker chosen individually should therefore allow the selection of transformed cells over cells which lack the DNA introduced.

Within the plant, the transformed cells grow in the customary manner (see also McCormick et al., Plant Cell Reports 5 (1986), 81–84). The resulting plants can be grown normally and hybridized with plants which have the same transformed germ plasm or other germ plasm. The resulting hybrid individuals have the corresponding phenotype properties. Seeds may be obtained from the plant cells. Two or more generations should be grown in order to ensure that the phenotype characteristic is stably retained and inherited. Also, seeds should be harvested in order to ensure that the phenotype in question or other characteristics have been retained.

EXAMPLES

The examples which follow are intended to illustrate the invention and do not constitute any restriction whatsoever.

1. Cloning Methods

The vector pBluescript II SK (Stratagene) was used for cloning in *E.coli*.

2. Bacterial Strains

The *E. coli* strain DH5α (Bethesda Research Laboratories, Gaithersburg, USA) was used for the Bluescript vector and for the antisense constructs. The *E. coli* strain XL1-Blue was used for the in vivo excision.

3. Transformation of Immature Wheat Embryos

| Media | | |
|---|---|---|
| MS: | 100 ml/l macrosalt<br>1 ml/l microsalt<br>2 ml/l Fe/NaEDTA<br>30 g/l sucrose | (D. Becker and H. Lörz, Plant Tissue Culture Manual (1996), B 12:1–20) |
| #30: | MS + 2,4-D (2 mg/l) | |
| #31: | MS + 2,4-D (2 mg/l) + phosphinothricin (PPT, active component of herbicide BASTA (2 mg/l)) | |
| #32: | MS + 2,4-D (0.1 mg/l) + PPT (2 mg/l) | |
| #39: | MS + 2,4-D (2 mg/ml) + of each 0.5 N mannitol/sorbitol | |

The media stated were brought to pH 5.6 using KOH and solidified using 0.3% Gelrite.

The method for transforming immature wheat embryos was developed and optimized by Becker and Lörz (D. Becker and H. Lörz, Plant Tissue Culture Manual (1996), B12: 1 to 20).

In the experiments described hereinbelow, the procedure developed by Becker and Lörz (loc. Cit) was adhered to.

For the transformation, ears with caryopses of developmental stage 12 to 14 days after anthesis were harvested and surface-sterilized. The isolated scutella were plated onto induction medium #30 with the embryo axis orientated toward the medium.

After preculture for 2 to 4 days (26° C., in the dark), the explants are transferred to medium #39 for the osmotic preculture (2 to 4 h, 26° C., in the dark).

For the biolistic transformation, approx. 29 μg of gold particles on which a few μg of the target DNA had previously been precipitated were employed per shot. Since the experiments carried out are cotransformants, the target DNA composed of the target gene and a resistance marker gene (bar gene) in the ratio 1:1 is added to the precipitation batch.

4. DIG Labeling of DNA Fragments

DNA fragments employed as screening probes were labeled via a specific PCR with the incorporation of DIG-labeled dUTP (Boehringer Mannheim, Germany).

Media and Solutions Used in the Examples:

| 20 × SSC | 175.3 g NaCl |
| --- | --- |
| | 88.2 g sodium citrate |
| | twice-distilled H₂O to 1000 ml |
| | 10 N NaOH to pH 7.0 |

Plasmid pTaSU 8A was deposited at the DSMZ in Braunschweig, Federal Republic of Germany, as specified in the Budapest Treaty under the No. DSM 12795, and plasmid pTaSU 19 under the No. DSM 12796.

EXAMPLE 1

Identification, Isolation and Characterization of a cDNA Encoding an Isoamylase ("Sugary" Homolog) from Wheat (*Triticum aestivum* L., cv Florida)

To identify a cDNA which encodes a wheat isoamylase isoform (sugary), a heterologous screening strategy was followed. To this end, a wheat cDNA library was screened with a maize sugary probe.

The probe (sugary probe) was isolated from a maize cDNA library by means of specific primers using PCR amplification. The maize cDNA library was cloned from poly(A)+RNA from a mixture of equal amounts of 13-, 17-, 19-, 20-, 22-, 25- and 28-day (DAP) old caryopses in a Lambda Zap II vector following the manufacturer's instructions (Lambda ZAP II-cDNA Synthesis Kit Stratagene GmbH, Heidelberg, Germany). In all the caryopses used, with the exception of the 13-day-old kernels, the embryo had been removed prior to isolating the RNA.

The DNA fragment employed as a probe for screening the wheat cDNA library was amplified with the following primers:

```
sulp-1:
5'-AAAGGCCCAATATTATCCTTTAGG-3'      (SEQ ID NO:4)

sulp-2:
5'-GCCATTTCAACCGTTCTGAAGTCGGGAAGTC-3'  (SEQ ID NO:5)
```

The template employed for the PCR reaction was 2 µL of the amplified maize cDNA library. Furthermore, the PCR reaction contained 1.5–3 mM MgCl₂, 20 mM Tris-HCl (pH 8.4), 50 mM KCl, 0.8 mM dNTP mix, 1 µM primer sulp-1a, 1 µM primer sulp-2 and 2.5 units Taq polymerase (recombinant, Life Technologies).

The amplification was carried out using a Trioblock from Biometra following the scheme: 4 min/95° C.; 1 min/95° C., 45 sec/58° C.; 1 min 15 sec/72° C.; 30 cycles 5 min/72° C. The amplified DNA band of approx. 990 bp was separated in an agarose gel and excised. A second amplification was [lacuna] from this fragment following the scheme as described above. The 990 bp fragment obtained from this second amplification was cleaved with the restriction enzyme BAM HI into a 220 bp and a 770 bp fragment. After the sugary fragment had again been separated in an agarose gel, the band excised and the fragment isolated, the probe was DIG-labeled. 500 ng of sugary fragment were employed for the random-prime labeling with digoxygenin. 10 µl of random primer were added to the fragment to be labeled and the reaction was heated for 5 min at 95–100° C. After heating, 0.1 mM dATP, 0.1 mM dGTP, 0.1 mM dCTP and 0.065 mM dTTP and 0.035 mM digoxygenin-11-dUTP (Boehringer Mannheim) and Klenow buffer (standard) and 1 unit of Klenow polymerase were added. The reaction was allowed to proceed at RT (room temperature) overnight. To check the labeling, a dot test was carried out following the manufacturer's instructions ("The DIG System User's Guide for Filter Hybridization" by Boehringer, Mannheim, Germany).

The wheat cDNA library was synthesized from poly(A)+ RNA of approx. 21-day ("starchy" endosperm) old caryopses in a Lamda Zap II vector following the manufacturer's instructions (Lambda ZAP II-cDNA Synthesis Kit, Stratagene GmbH, Heidelberg). After determination of the titer of the cDNA library, a primary titer of 1.26×10⁶ pfu/ml was determined.

To screen the wheat cDNA library, approx. 350,000 phages were plated out. The phages were plated out and the plates blotted by standard protocols. The filters were pre-hybridized and hybridized in 5×SSC, 3% blocking (Boehringer, Mannheim), 0.2% SDS, 0.1% sodium lauryl-sarcosin and 50 µg/ml herring sperm DNA at 55° C. 1 ng/ml of the labeled sugary probe was added to the hybridization solution and the hybridization was incubated overnight. The filters were washed 2×5 mins in 2×SSC, 1% SDS at RT; 2×10 min in 1×SSC, 0.5% SDS at 55° C.; 2×10 min in 0.5×SSC, 0.2% SDS at 55° C. Positive clones were singled out by further screening cycles. Single clones were obtained via in vivo excision as pBluescript SK phagemids (procedure analogous to the manufacturer's instructions; Stratagene, Heidelberg, Germany).

After the clones had been analyzed via minipreps and restriction of the plasmid DNA, clone pTaSU-19 was deposited at the DSMZ Deutsche Sammlung für Mikroorganismen und Zelikulturen GmbH under the number DSM 12796 and analyzed in greater detail.

EXAMPLE 2

Sequence Analysis of cDNA Insertions of Plasmids pTaSU19

The plasmid DNA was isolated from clone pTaSU19 and the sequence of the cDNA insertions determined by means of the dideoxynucleotide method (Sanger et al., Proc. Natl. Acad. Sci. USA 74 (1977), 5463–5467).

The insertion of clone TaSU-19 is 2997 bp in length and constitutes a partial cDNA. The nucleotide sequence is shown under SEQ ID NO:2. A comparison with already published sequences revealed that the sequence shown under SEQ ID NO:2 encompasses a coding region which has homologies to isoamylases from other organisms.

Sequence analysis also reveals that two introns are located in the cDNA sequence in position 297–396 (intron 1) and 1618–2144 (intron 2). If these introns are removed, a protein sequence may be derived which exhibits homologies to the protein sequences of isoamylases of other organisms. The amino acid sequence which corresponds to the coding regions of SEQ ID NO:2 is shown under SEQ ID NO:3.

EXAMPLE 3

Generation of the Plant Transformation Vector pTa-alpha-SU19

To express an antisense RNA corresponding to the TaSU19-cDNA, the plant transformation vectors pTa-alpha-SU19 were constructed on the basis of the basic plasmid pUC19 by linking the cDNA insertion of plasmid pTa-alpha-SU19 in antisense orientation to the 3' end of the ubiquitin promoter. This promoter is composed of the first untranslated exon and the first intron of the maize ubiquitin 1 gene (Christensen A. H. et al., Plant Molecular Biology 19 (1992), 675–689). Parts of the polylinker and the NOS terminator are derived from plasmid pAct1.cas (CAMBIA, TG 0063; Cambia, GPO Box 3200, Canberra ACT 2601, Australia). Vector constructs with this terminator and constructs based on pAct1.cas are described by MCElroy et al. (Molecular Breeding 1 (1995), 27–37). The vector thus formed was termed pUbi.cas.

The vector was cloned by restricting a 2 kb fragment from clone Ta-SU19 with the restriction enzyme Xba I. The fragment was filled up at the ends by means of Klenow reaction and subsequently ligated into the Sma I cloning site of the expression vector pUbi.cas.

The resulting expression vector is termed Ta-alpha-SU 19 and is used as described above for transforming wheat.

EXAMPLE 4

Isolation and Characterization of a Further cDNA Encoding an Isoamylase (Sugary 1 Homolog) from Wheat (*Triticum aestivum L.*, cv Florida)

A wheat cDNA library was screened with a sugary probe which represents a part of clone pTaSU19, viz. positions 489–1041 of Seq ID No. 1.

The wheat-specific digoxygenin-labeled sugary probe employed for screening the cDNA library was prepared by means of PCR amplification. The primers employed in this reaction were:

```
SUSO1:
5'-GCT TTA CGG GTA CAG GTT CG-3',  and   (SEQ ID NO:8)

SUSO2:
5'-AAT TCC CCG TTT GTG AGC-3'            (SEQ ID NO:9)
```

1 ng of plasmid pTaSU19 was employed in the reaction as template. In addition, the PCR reaction contained in each case 300 nM of the primers SUSO1 and SUSO2, in each case 100 µM of the nucleotides dATP, dGTP, dCTP, 65 µM dTTP, 35 µM digoxygenin-11-dUTP (Boehringer Mannheim), 1.5 mM MgCl$_2$, and 2.5 U (units) Taq polymerase and 10 µl of 10-fold concentrated Taq polymerase reaction buffer (both Life Technologies). The final volume of the reaction was 100 µl. The amplification was performed in a PCR apparatus (TRIO® Thermoblock, Biometra) with the following temperature regime: 3 min at 95° C. (once); 45 sec at 95° C.—45 sec at 55° C.—2 min at 72° C. (30 cycles); 5 min at 72° C. (once). A 553 bp DNA fragment resulted. The incorporation of dogoxygenin-11-dUTP into the PCR product was revealed owing to the reduced mobility in the agarose gel in comparison with the product of a controlled reaction without digoxygenin-11-dutp.

The caryopses-specific wheat cDNA library of Example 1 was screened with the resulting digoxygenin-labeled probe.

The hybridization step was performed overnight in 5×SSC, 0.2% SDS, 0.1% sodium laurylsarcosin and 50 µg/ml herring sperm DNA at 68° C. in the presence of 1 ng/ml of the digoxygenin-labeled probe. After the hybridization, the filters were washed as follows: 2×5 min in 2×SSC, 1% SDS at RT; 2×10 min in 1×SSC, 0.5% SDS at 68° C.; 2×10 min in 0.5×SSC, 0.2% SDS at 68° C. Positive clones were singled out by at least two further screening cycles. Plasmids were obtained from the phage clones pBluescript SK via in vivo excision (protocols in accordance with the manufacturer's instructions; Stratagene, Heidelberg, Germany). After restriction analysis it clones obtained, clone pTaSU8A was deposited at the Deutsche Sammlung für Mikroorganismen und Zelikulturen under the number DSM 12795 and studied in greater detail.

EXAMPLE 5

Sequence Analysis of the cDNA Insert in Plasmid pTaSU8A

The nucleotide sequence of the cDNA insert in plasmid pTaSU8A was determined by means of the dideoxynucleotide method (SEQ ID NO:6).

The insertion of clone pTaSU8A is 2437 bp in length and constitutes a partial cDNA. A comparison with already published sequences reveals that the sequence shown under SEQ ID NO:6 comprises a coding region which has homologies to isoamylases from other organisms. Equally, the protein sequence derived from the coding region of clone pTaSU8A and shown in SEQ ID NO:7 exhibits homologies to the protein sequences of isoamylases of other organisms. Upon comparison of the sequences of clones pTaSU19 (SEQ ID NO:1) and pTaSU8A (SEQ ID No:6), a similarity of 96.8% results. Most of the differences regarding the sequences are in the 3'-untranslated region of the cDNAs. The remaining differences regarding the sequences in the coding region lead to different amine acids at a total of 12 positions of the derived protein sequences SEQ ID NOs:3 and 7. The cDNAs contained in pTaSU19 and pTaSU8A are not identical and encode isoforms of the wheat isoamylase.

EXAMPLE 6

Generation of the Plant Transformation Vector pTa-alpha-SU8A

To express an antisense RNA corresponding to the TaSU8A cDNA, the plant transformation vector pTa-alpha-SU8A was constructed on the basis of the basic plasmid pUC19 by linking a part of the TaSU8A cDNA generated by PCR amplification in antisense orientation to the 3' end of the ubiquitin promoter. This promoter is composed of the first untranslated exon and the first intron of the maize ubiquitin I gene (Christensen A. H. et al., Plant Mol. Biol 1 (1992), 675–689). Parts of the polylinker and the NOS terminator are derived from plasmid pAct1. cas (CAMBIA, TG 0063; Cambia, GPO Box 3200, Canberra ACT 2601, Australia). Vector constructs with this terminator and constructs based on pAct1. cas are described by McElroy et al. (Molecular Breeding 1 (1995), 27–37). The vector containing ubiquitin promoter, polylinker and NOS terminator and based on pUC19 was termed pUbi.cas.

To clone pTa-alpha-SU8A, an approx. 2.2 kb portion of the TaSU8A cDNA, viz. positions 140–2304 of SEQ ID NO:6 was amplified by means of PCR.

The primers employed in this reaction were:

```
SUEX3:
5'-GCG GTA CCT CTA GGA GGA GAT ATA    SEQ ID NO:10
CAT ATG GCG GAG GAC AGG TAC GCG CTC-
3', and

SUEX4:
5'-GCT CGA GTC GAC TCA AAC ATC AGG    SEQ ID NO:11
GCG CAA TAC-3'.
```

1 ng of plasmid pTaSU8A was employed in the reaction as template. In addition, the PCR reaction contained: in each case 300 nM of the primers SUEX3 and SUEX4, in each case 200 µM of the nucleotides dATP, dGTP, dCTP and dTTP, 1.6 mM MgCl₂, 60 mM Tris-SO₄ (pH 9.1), 18 mM (NH₄)₂SP₄ and 1 µl of Elongase® enzyme mix (mixture of Taq polymerase and DNA polymerase, Life Technologies). The final volume of the reaction was 50 µl. Amplification was performed in a PCR apparatus (TRIO® Thermoblock, Biometra) with the following temperature regime: 1 min at 94° C. (once); 30 sec at 95° C.—30 sec at 55° C.—2 min 30 sec at 68° cycles); 10 min at 68° C. (once). The reaction gave rise to a DNA fragment 2205 bp in length.

The 2.2 kb product was restricted with KpnI and SalI and ligated into the expression vector pUbi.cas which had previously been cleaved with KpnI and SalI. The resulting plant transformation vector was termed pTa-alpha-SU8A and used as described above for transforming wheat.

We claim:

1. A vector containing an isolated nucleic acid molecule encoding a protein with the function of a wheat isoamylase, selected from the group consisting of
   (a) a nucleic acid molecule encoding a protein comprising the amino acid sequence shown under SEQ ID NO:3,
   (b) a nucleic acid molecule comprising the nucleotide sequence shown under SEQ ID NO:2 or a ribonucleotide sequence corresponding hereto;
   (c) a nucleic acid molecule which hybridizes under stringent conditions with a nucleic acid molecule mentioned under (a) or (b) or is complementary thereto, wherein hybridization comprise a hybridization temperature of 68° C., a hybridization buffer salt concentration of 5×SSC, a wash temperature of 68° C., and a wash buffer salt concentration of 0.5×SSC; and
   (d) a nucleic acid molecule whose nucleotide sequence deviates from the sequence of a nucleic acid molecule mentioned under (a), (b) or (c) owing to the degeneracy of the genetic code,
the nucleic acid molecule mentioned under (a), (c) and (d) having sequence identity of over 90% with SEQ ID NO:2, wherein said nucleic acid molecule is linked in sense orientation to regulatory elements, which ensure the synthesis of an untranslatable RNA in prokaryotic or eukaryotic cells.

2. A vector containing an isolated nucleic acid molecule encoding a protein with the function of a wheat isoamylase, selected from the group consisting of
   (a) a nucleic acid molecule encoding a protein comprising the amino acid sequence shown under SEQ ID NO:3,
   (b) a nucleic acid molecule comprising the nucleotide sequence shown under SEQ ID NO:2 or a ribonucleotide sequence corresponding hereto;
   (c) a nucleic acid molecule which hybridizes under stringent conditions with a nucleic acid molecule mentioned under (a) or (b) or is complementary thereto, wherein hybridization comprise a hybridization temperature of 68° C., a hybridization buffer salt concentration of 5×SSC, a wash temperature of 68° C., and a wash buffer salt concentration of 0.5×SSC; and
   (d) a nucleic acid molecule whose nucleotide sequence deviates from the sequence of a nucleic acid molecule mentioned under (a), (b) or (c) owing to the degeneracy of the genetic code, the nucleic acid molecule mentioned under (a), (c) and (d) having sequence identity of over 90% with SEQ ID NO:2, wherein said nucleic acid molecule is linked in antisense orientation to regulatory elements, which ensure the synthesis of an untranslatable RNA in prokaryotic or eukaryotic cells.

3. A host cell which is transformed with the vector of claim 1 or 2 or a cell which is derived from the host cell and comprises the vector of claim 1 or 2.

4. A process for generating a transgenic plant tell, wherein the vector of claim 1 or 2 is integrated into the genome of a plant cell.

5. A transgenic plant cell that has been transformed with the vector of claim 1 or 2 or a cell which is derived from the transgenic plant cell and comprises the vector of claim 1 or 2.

6. A plant containing the plant cell of claim 5.

7. A process for generating a transgenic plant, wherein (a) the vector of claim 1 or 2 is integrated into the genome of a plant cell and (b) an intact plant is regenerated from said plant cell.

8. A transgenic plant generated by the process of claim 7.

9. The plant of claim 6, which is a crop plant.

10. The plant of claim 6, which is a starch-synthesizing or starch-storing plant.

11. A propagation material of the plant of claim 6.

* * * * *